US012558417B2

(12) United States Patent     (10) Patent No.:   US 12,558,417 B2
Lee et al.                 (45) Date of Patent:     Feb. 24, 2026

(54) HEPATITIS A VIRUS PREPARATION METHOD AND HEPATITIS A VIRUS PREPARED ACCORDING TO METHOD

(71) Applicant: SK BIOSCIENCE CO., LTD., Seongnam-si (KR)

(72) Inventors: Jung-eun Lee, Seongnam-si (KR); Soo-young Kim, Seongnam-si (KR); Seo Young Cho, Seongnam-si (KR); Hun Kim, Seongnam-si (KR); Kun Se Lee, Seongnam-si (KR); Sujeen Lee, Seongnam-si (KR)

(73) Assignee: SK BIOSCIENCE CO., LTD., Seongnam-si (KR)

( * ) Notice: Subject to any disclaimer, the term of this patent is extended or adjusted under 35 U.S.C. 154(b) by 624 days.

(21) Appl. No.: 17/787,925

(22) PCT Filed: Dec. 18, 2020

(86) PCT No.: PCT/KR2020/018703
§ 371 (c)(1),
(2) Date: Jun. 21, 2022

(87) PCT Pub. No.: WO2021/125891
PCT Pub. Date: Jun. 24, 2021

(65) Prior Publication Data
US 2025/0170234 A1     May 29, 2025

(30) Foreign Application Priority Data
Dec. 19, 2019    (KR) ........................ 10-2019-0171279

(51) Int. Cl.
| | |
|---|---|
| *A61K 39/29* | (2006.01) |
| *A61K 39/00* | (2006.01) |
| *A61P 31/14* | (2006.01) |
| *C12N 5/071* | (2010.01) |
| *C12N 7/00* | (2006.01) |
| *C12N 15/86* | (2006.01) |

(52) U.S. Cl.
CPC ............. *A61K 39/29* (2013.01); *A61P 31/14* (2018.01); *C12N 5/0686* (2013.01); *C12N 7/00* (2013.01); *C12N 15/86* (2013.01); *A61K 2039/5252* (2013.01); *A61K 2039/5254* (2013.01); *C12N 2770/32421* (2013.01); *C12N 2770/32443* (2013.01); *C12N 2770/32451* (2013.01); *C12N 2830/50* (2013.01); *C12N 2830/52* (2013.01)

(58) Field of Classification Search
None
See application file for complete search history.

(56) References Cited

U.S. PATENT DOCUMENTS

| | | |
|---|---|---|
| 5,731,187 A | 3/1998 | Fanget et al. |
| 6,680,060 B2 | 1/2004 | Funkhouser et al. |

FOREIGN PATENT DOCUMENTS

| | | |
|---|---|---|
| KR | 10-2015-0136767 A | 12/2015 |

OTHER PUBLICATIONS

FDA. Center for Drug Evaluation and Research , 8-page printout. https://www.fda.gov/drugs/drug-approvals-and-databases/drugsfda-glossary-terms. Retrieved May 19, 2025. Published Nov. 14, 2017. (Year: 2017).*
CDC. Hepatitis A Vaccine Administration. 3-page printout, accessed on May 20, 2025 at https://www.cdc.gov/hepatitis-a/hcp/vaccine-administration/index.html. Published Jan. 31, 2025. (Year: 2025).*
GenBank accession NC_001489.1 (published Aug. 13, 2018). (Year: 2018).*
Beard et al. J Virol. Feb. 2001;75(3):1414-26. doi: 10.1128/JVI.75.3.1414-1426.2001. PMID: 11152515. (Year: 2001).*
Lemon, Stanley M. et al. "Antigenic and Genetic Variation in Cytopathic Hepatitis A Virus Variants Arising during Persistent Infection: Evidence for Genetic Recombination," Journal of Virology, Apr. 1991, vol. 65, No. 4, p. 2056-2065 (11 pages).
McKnight, Kevin L. "Hepatitis A Virus Genome Organization and replication Strategy," Cold Spring Harb Perspect Med 2018 (19 pages).
International Search Report received in PCT/KR2020/018703 issued Mar. 31, 2021.
NCBI, GenBank Accession No. KP879216.1, Hepatitis A virus isolate 18f, complete genome, Jun. 21, 2017.
Tan, Chee Wah, Enterovirus A71 DNA-launched infectious clone as a robust reverse genetic tool, PloS one, DOI:10.1371/journal.pone.0162771, Sep. 12, 2016.

* cited by examiner

*Primary Examiner* — Benjamin P Blumel
*Assistant Examiner* — Jeffrey Mark Sifford
(74) *Attorney, Agent, or Firm* — Meunier Carlin & Curfman LLC

(57) ABSTRACT

The present invention relates to a hepatitis A virus production method and hepatitis A virus produced according to the method, and, more specifically, to: a hepatitis A virus production method and hepatitis A virus produced according to the method, the method comprising the step of infecting a host cell with a virus obtained by transforming a host cell with a vector comprising an expression cassette, which comprises a hepatitis A virus gene, for hepatitis A virus preparation, and subculturing same.

22 Claims, 14 Drawing Sheets
Specification includes a Sequence Listing.

FIG. 1

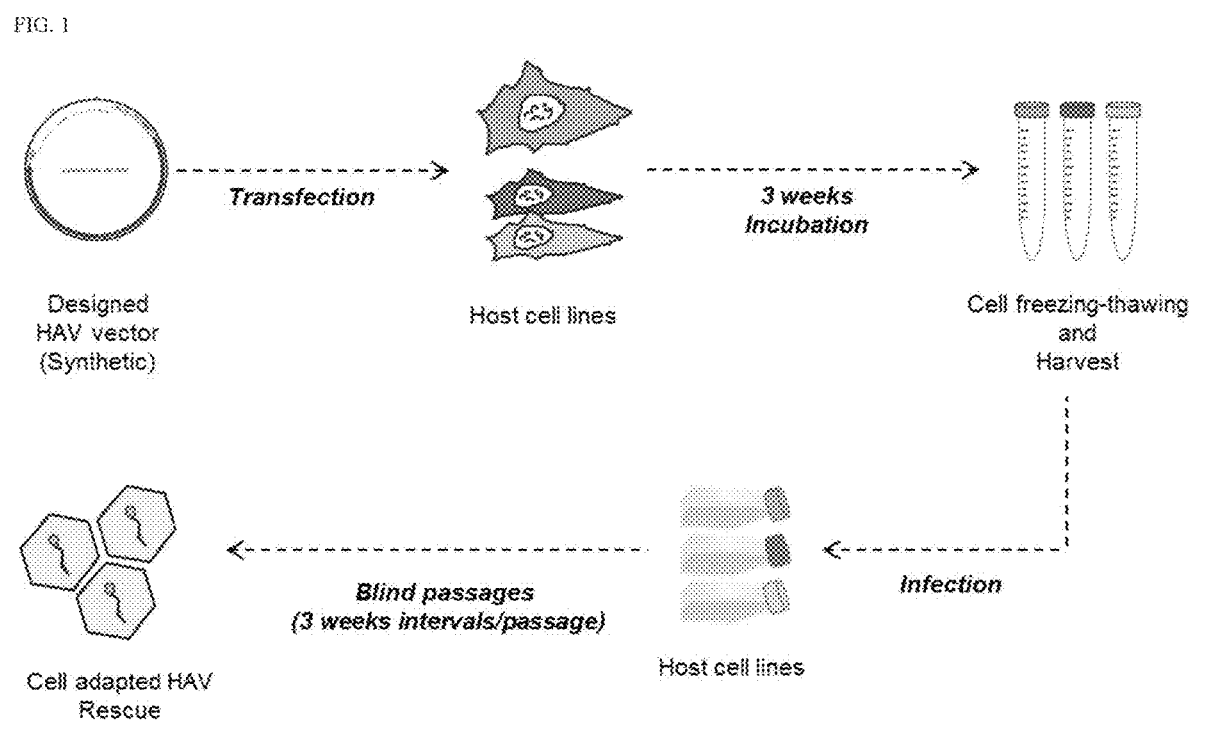

Designed
HAV vector
(Synthetic)

Transfection

Host cell lines 3 weeks
Incubation

Cell freezing-thawing
and
Harvest

Infection

Host cell lines

Blind passages
(3 weeks intervals/passage)

Cell adapted HAV
Rescue

ELISA analysis: HAV Ag quantification results in cell lysate (P6 blind passage)

| Host cells | Blind passage | HAV Ag results in P6 cell lysates (IU/mL) |
|------------|---------------|---------------------------------------------|
| MA104      | P6            | 2371                                        |
| Vero       | P6            | 586                                         |
| SF-Vero    | P6            | 926                                         |

Immunofluorescence assay results: Harvest cell lysate (P6) infection at 7 days post-infection virus passages (SF-Vero)

| virus passages | 1 | 2 | 3 | 4 | 5 | 6 | 7 | 8 | 9 | 10 |
|---|---|---|---|---|---|---|---|---|---|---|
| supernatant | 1.650 | 1.552 | 1.258 | 1.115 | 1.559 | 1.102 | 1.279 | 1.458 | 1.298 | 1.420 |
| cell lysate | 3.106 | 3.884 | 3.435 | 3.740 | 3.800 | 3.900 | 3.814 | 3.762 | 3.735 | 3.747 | virus passages (MRC-5)

| virus passages | 1 | 2 | 3 | 4 | 5 | 6 | 7 | 8 | 9 | 10 |
|---|---|---|---|---|---|---|---|---|---|---|
| supernatant | 0.134 | 0.560 | 0.060 | 0.033 | 0.280 | 0.283 | 0.029 | 0.223 | 0.047 | 0.286 |
| cell lysate | 0.000 | 1.332 | 1.256 | 2.497 | 2.812 | 1.409 | 3.293 | 2.317 | 2.954 | 2.511 |

| dpi | 3 | 7 | 10 | 14 | 17 | 21 | 24 | 28 |
|---|---|---|---|---|---|---|---|---|
| cell lysate (IU) ◆ | 76.0 | 834.7 | 936.0 | 2213.3 | 3151.3 | 3537.3 | 3230.0 | 3062.7 |
| supernatant (IU) ※ | 0.0 | 191.0 | 148.5 | 272.0 | 304.0 | 706.5 | 697.5 | 801.8 |

| Group | MA104 | Vero | SF-Vero |
|---|---|---|---|
| (A) | 87255.0 | 7020.0 | 11260.8 |
| (B) | 133368.8 | 32962.5 | 28231.9 | anti-HAV Antidbody Titer

SEQUENCE LISTING

<160> NUMBER OF SEQ ID NOS: 8

<210> SEQ ID NO 1
<211> LENGTH: 7487
<212> TYPE: DNA
<213> ORGANISM: Artificial Sequence
<220> FEATURE:
<223> OTHER INFORMATION: Hepatitis A Virus Polyprotein Nucleotide
      Sequence

<400> SEQUENCE: 1

```
ttcaagaagg gtctccggga atttccggag tccctcttgg aagtccatgg tgaggggact      60
tgatacctca ccgccgtttg cctaggctat aggctaaatt ttcccttttcc cttttcccctt     120 tcctattccc tttgttttgc ttgtaaatat tgatttgtaa atattgattc ctgcaggttc     180
agggttctta aatctgtttc tctataagaa cactcatttc acgctttctg tcttcttttct     240 tccagggctc tccccttgcc ctaggctctg gccgttgcgc ccggcggggt caactccatg     300
attagcatgg agctgtagga gtctaaattg gggacacaga tgtttggaac gtcaccttgc     360
agtgttaact tggctttcat gaatctcttt gatcttccac aaggggtagg ctacgggtga     420
aacctcttag gctaatactt ctatgaagag atgccttgga tagggtaaca gcggcggata     480
ttggtgagtt gttaagacaa aaaccattca acgccggagg actgactctc atccagtgga     540
tgcattgagt ggattgactg tcggggctgt ctttaggctt aattccagac ctctctgtgc     600
ttggggcaaa catcatttgg ccttaaatgg gattctgtga gaggggatcc ctccattgcc     660
agctggactg ttctttgggg ccttatgtgg tgtttgccgc tgaggtactc aggggcattt     720
aggtttttcc tcattcttaa ataataatga acatgtctag acaaggtatt ttccagactg     780
ttgggagtgg tcttgaccac atcctgtctt tggcagacat tgaggaagag caaatgattc     840
aatcagttga taggactgca gtgactggtg cttcttattt tacttctgtg gatcaatctt     900
cagttcatac agctgaggtt ggatcacacc aggttgaacc tttgagaacc tctgttgata     960
aacccggttc aaagaggact caggagagaa attttttctt gattcattct gcagattggc    1020
ttactacaca tgctctttttc catgaagttg caaaattgga tgtggtgaaa ttattataca    1080
atgagcagtt tgctgttcaa gggttgttga gataccatac atatgcaaga tttggcattg    1140
aaattcaagt tcagataaac cctacacctt ccaacagggg gggattgatc tgtgctatgg    1200
ttcctggtga ccagagctat ggttctatag catcattgac tgtttatcct catggtttgt    1260
taaattgcaa tattaacaat gtggttagaa taaaggttcc atttatttac acaagaggtg    1320
cttaccactt aaagatcca caatacccag tttgggaatt gacaattaga gtttggtcag    1380
aattaaatat tgggacagga acttcagctt atacttcact caatgtttta gctagattta    1440
cagatttgga gttgcatgga ttaactcctc tttctacaca aatgatgaga aatgaattta    1500
gggtcagtac tactgagaat gtggtgaatc tgtcaaatta tgaagatgca agagcaaaga    1560
tgtcttttgc tttggatcag gaagattgga atctgatcc gtcccagggt ggtgggatca    1620
aaattactca ttttactact tggacatcta ttccaacttt ggctgctcag tttccattta    1680
atgcttcaga ctcagttggt caacaaatta agttattcc agttgaccca tattttttcc    1740
aaatgacaaa taaaaatcct gaccaaaaat gtataactgc tttggcttct atttgtcaga    1800 tgtttgtgtttt ttggagagga gatcttgtct ttgattttca agttttttccc accaaatatc    1860
```

-continued

```
attcaggtag attactgttt tgttttgttc ctggcaatga gctaatagat gtttctggaa    1920
tcacattaaa gcaagcaact actgctcctt gtgcagtaat ggatattaca ggagtgcagt    1980
caactttgag atttcgtgtt ccctggattt ctgacactcc ttacagagtg aacaggtata    2040
caaagtcagc acatcagaaa ggtgagtaca ctgccattgg gaagcttatt gtgtattgtt    2100
ataacagatt gacctctcct tctaacgttg cttcccatgt cagagtgaat gtttatcttt    2160
cagcaattaa cttggaatgt tttgctcctc tttatcatgc tatggatgtt actacacaag    2220
ttggagatga ttctggaggt ttttcaacaa cagtttctac agaacagaat gttccagatc    2280
cccaagttgg tataacaacc atgaaagatt tgaaaggaaa agctaacaga gggaaaatgg    2340
atgtttcagg agtacaagca cctgtgggag ctatcacaac aattgaggat ccagtttttag   2400 caaagaaagt acctgagaca tttcctgaat tgaaacctgg agaatccaga catacatcag    2460
atcatatgtc catctacaag tttatgggaa ggtctcattt cttgtgcact tttacattca    2520
attcaaataa taaagagtac acatttccta taaccttgtc ttcaacctct aatcctcctc    2580
atggtttgcc atcaacactg aggtggtttt tcaacttgtt tcagttgtat agagggcctt    2640
tagatctgac aattattatt acaggagcaa ctgatgtaga tggcatggcc tggtttactc    2700
cagtaggtct tgccgttgat actccttggg tagagaagga gtcagctttg tctattgact    2760
acaaaactgc tcttggagct gtcagattta acacaaggag aacagggaac attcagatta    2820
gattaccatg gtattcttat ttatatgctg tgtctggagc actggatggt ttgggtgaca    2880
agacagattc tacatttgga ttggtttcta ttcagattgc aaattacaat cattctgatg    2940
aatacttgtc ttttagttgt tatttgtctg tcacagaaca atcagagttt tattttccca    3000
gagctccatt gaactcaaat gccatgttac ccactgaatc aatgatgagc agaattgcag    3060
ctggagactt ggagtcatca gtggatgatc ctagatcaga ggaagataaa agatttgaga    3120
gtcatataga atgcaggaag ccatataaag aactgagatt agaagttggg aaacaaagac    3180
tcaagtatgc tcaggaagaa ttgtcaaatg aagtacttcc accccctagg aaaatgaagg    3240
gactgttttc acaagccaat atttctcttt tttatactga ggagcatgaa atgatgaagt    3300
tttcctggag aggtgtgact gctgatacta gagctttaag gaggtttgga ttctctttgg    3360
ccgcaggcag aagtgtgtgg actcttgaaa tggatgctgg ggttcttact gggagactga    3420
ttagattgaa tgatgagaaa tggacagaaa tgaaggatga caagattgtt tcattgattg    3480
aaaagtttac aagtaacaaa tattggtcca aagtgaattt cccacatggg atgttggatc    3540
ttgaagaaat tgctgccaat tctaaggatt ttcctaacat gtctgaaacg gatttgtgtt    3600
tcttgctgca ttggttaaat ccaaagaaaa ttaatttagc agatagaatg cttggattgt    3660
ctggagttca ggaaattaaa gaacaaggtg ttggattaat agcagagtgt agaactttct    3720
tacattctat tgctggaact ttaaaatcta tgatgtttgg atttcatcat tctgtgactg    3780
ttgaaattat aaacactgtg ctctgttttg ttaagagtgg aattttgctt tatgtaatac    3840
aacaattgaa tcaggatgaa cattctcaca taattggtct gttgagagtc ttgaattatg    3900
tagatattgg ttgttcagtt atttcatgtg gcaaagtttt ttccaaaatg ctggaaacag    3960
tctttaattg gcaaatggac tccagaatga tggagttaag gactcagagt ttttccaact    4020
ggttaagaga tatttgttct gggatcacca tttttaaaaa cttcaaggat ggaatttgtt    4080
ggctttatac aaaattaaag gactttttatg aagtgaatta tggcaagaag aaggacattt    4140
taaatattct taaagataac caacaaaaaa tagagaaagc cattgaggaa gccgataaat    4200
tttgcatttt gcaaatccaa gatgtggaaa aatctgaaca gtatcagaaa ggggttgact    4260
```

```
tgatacaaaa attgagaact gtttattcaa tggctcaggt tgatccaaat ttaatggttc      4320
atttgtcacc tttgagagat tgtatagcaa gagttcatca gaaacttaaa aaccttggat      4380
ttataaatca ggcaatggta acgagatgtg agccagttgt ttgttattta catggcaaaa      4440 gaggggggagg aaagagctta acatcaattg cattggcaac caaaatttgt aaacattatg      4500
gtgttgagcc tgaaaagaat atctatacta aacctgtggc ttcagattac tgggatggat      4560
atagtggaca attagtttgc atcattgatg atattggcca aaacacaaca gatgaggact      4620
ggtcagattt ttgtcagtta gtgtcaggat gtccaatgag attaaacatg gcctctcttg      4680
aggagaaggg taggcatttt tcttctcctt ttataatagc aacttcaaat tggtcaaatc      4740
caagtccaaa aacagtttat gttaaggaag caattgaccg cagactccat ttcaaggttg      4800
aagttaaacc tgcttcattt ttcaaaaatc ctcacaatga tatgttgaat gttaatttag      4860
ctaaaacaaa tgatgcaatc aaagatatgt cttgtgttga tttgataatg gatggacata      4920
atgtttcatt gatggatttg ctcagttctt tagtcatgac agttgatatt agaaaacaaa      4980
acatgactga attcatggag ttgtggtctc agggaatttc agatgataat gatagtgcag      5040
tagctgagtt tttccagtct tttccatctg gtgaaccatc gaactctaaa ttatctggct      5100
ttttccaatc tgttactaat cacaagtggg ttgctgtggg agctgcagtt ggcattcttg      5160
gagtgctcgt tggaggatgg gttgtgtata agcatttctc ccacaaagag gaagaaccaa      5220
tcccagctga aggggtatat catggtgtaa ctaagcccaa gcatgtgatt aaattagatg      5280
cagatccagt agaatctcag tcaactttgg aaatagcagg actggttagg aagaacttgg      5340
ttcagtttgg agttggagag aagaatggat gtgtgagatg ggttatgaat gccttgggag      5400
tgaaagatga ttggctgctt gtgccttccc atgcttataa atttgagaaa gattatgaaa      5460
tgatggagtt ttattttaat agaggtggaa cttactattc aatttcagct ggtaatgttg      5520
ttattcaatc tttggatgtg ggattccagg atgttgttct gatgaaggtt cctacaattc      5580
ctaagtttag agatattact gagcattta ttaagaaagg ggatgtgcct agagctttga      5640
atcgcctggc aacattagtg acaactgtaa atggaacccc tatgttaatt tctgagggcc      5700
cactaaagat ggaagagaaa gctacttatg ttcataagaa aaatgatggt acaacagttg      5760
atttaactgt ggatcaggca tggagaggaa aaggcgaagg tcttcctgga atgtgtggtg      5820
gggccttggt ttcatcgaat caatctatac agaatgcaat cttgggcatc catgttgctg      5880
gaggaaattc aattcttgtt gcaaaattgg ttactcaaga aatgttccaa aatattgata      5940
agaaaattga aagtcagaga attatgaaag tggagtttac tcagtgttca atgaatgtgg      6000
tctccaaaac gctttttaga aagagtccca tttatcatca cattgataaa accatgatta      6060
attttcctgc agctatgccc tttttctaaag ctgaaattga tccaatggct gtgatgttat      6120
ctaagtattc attacctatt gtagaagaac cagagggtta taagaggct tcaatttttt      6180 atcaaaataa aatagtgggt aagactcagt tagttgatga ttttctagat cttgatatgg      6240
ccattacagg ggccccagga attgatgcta tcaacatgga ttcatctcct ggatttcctt      6300
atgtccagga gaagttgacc aaaagagatt taatttggtt ggatgaaaat ggtttattgc      6360
tgggagttca tccaagattg gctcagagaa tcttattcaa tactgtcatg atggaaaatt      6420
gttctgattt ggatgttgtt tttacaacct gtccaaaaga tgaattgagg ccattagaga      6480
aagtgttgga atcaaaaaca agagctattg atgcttgtcc tctggattac acaattttgt      6540
gccgaatgta ttggggtcca gctattagtt attttcattt gaatccaggt ttccatacag      6600
```

```
gtgttgctat tggcatagat cctgataaac agtgggatga actatttaaa acaatgataa    6660
gattcggaga tgttggtctt gatttagatt tctctgcttt tgatgctagt cttagtccat    6720
ttatgattag agaagcaggt agaatcatga gtgaactatc tggaactcca tcccattttg    6780
gcacagctct tatcaatact atcatttatt ccaagcattt gctgtataac tgttgttacc    6840
atgtctgtgg ttcaatgccc tctgggtctc cttgtacagc tttgctaaat tcaattatta    6900
ataatgtcaa tttgtattat gtgttttcta agatatttgg aaagtctcca gttttctttt    6960
gtcaggcttt gaagattctc tgttatggag atgatgtttt aatagttttc tctcgagatg    7020
ttcagattga taatcttgat ttgattggac aaaaaaattgt agatgagttt aagaaacttg    7080
gcatgacagc tacttctgct gacaagaatg tacctcagct gaaaccagtt tcggaattga    7140
cttttctcaa aagatctttc aatttggtag aggatagaat tagacctgca atttcggaaa    7200
aaacaatttg gtctttaata gcatggcaga gaagtaacgc tgagtttgag cagaacttag    7260
aaaatgctca gtggtttgct tttatgcatg gctatgagtt ttatcagaaa ttctattatt    7320
ttgttcagtc ctgtttggag aaagagatga tagaatacag acttaaatct tatgattggt    7380
ggagaatgag attttatgac cagtgtttca tttgtgacct ttcatgattt gtttaaatga    7440
actttcttaa aatttctgag gtttgtttat ttcttttatc agtaaat              7487
```

<210> SEQ ID NO 2
<211> LENGTH: 646
<212> TYPE: DNA
<213> ORGANISM: Artificial Sequence
<220> FEATURE:
<223> OTHER INFORMATION: CMV immearly promoter - T7 promoter

<400> SEQUENCE: 2

```
acattgatta ttgactagtt attaatagta atcaattacg gggtcattag ttcatagccc      60
atatatggag ttccgcgtta cataacttac ggtaaatggc ccgcctggct gaccgcccaa     120 cgaccccgc ccattgacgt caataatgac gtatgttccc atagtaacgc caatagggac     180
tttccattga cgtcaatggg tggagtattt acggtaaact gcccacttgg cagtacatca     240
agtgtatcat atgccaagta cgccccctat tgacgtcaat gacggtaaat ggcccgcctg     300
gcattatgcc cagtacatga ccttatggga ctttcctact tggcagtaca tctacgtatt     360
agtcatcgct attaccatgg tgatgcggtt ttggcagtac atcaatgggc gtggatagcg     420
gtttgactca cggggatttc caagtctcca ccccattgac gtcaatggga gtttgttttg     480
gcaccaaaat caacgggact ttccaaaatg tcgtaacaac tccgccccat tgacgcaaat     540
gggcggtagg cgtgtacggt gggaggtcta tataagcaga gctctctggc taactagaga     600
acccactgct tactggctta tcgaaattaa tacgactcac tatagg                  646
```

<210> SEQ ID NO 3
<211> LENGTH: 35
<212> TYPE: DNA
<213> ORGANISM: Artificial Sequence
<220> FEATURE:
<223> OTHER INFORMATION: MCS sequence

<400> SEQUENCE: 3

```
gagctctcgc gaatgcatga tatcggatcc tcgag                              35
```

<210> SEQ ID NO 4
<211> LENGTH: 51
<212> TYPE: DNA
<213> ORGANISM: Artificial Sequence
<220> FEATURE:
<223> OTHER INFORMATION: HH ribozyme

<400> SEQUENCE: 4
ccttcttgaa ctgatgaggc cgaaaggccg aaaacccggt atcccgggtt c          51

<210> SEQ ID NO 5
<211> LENGTH: 68
<212> TYPE: DNA
<213> ORGANISM: Artificial Sequence
<220> FEATURE:
<223> OTHER INFORMATION: HDV ribozyme

<400> SEQUENCE: 5
ggccggcatg gtcccagcct cctcgctggc gccggctggg caacatgctt cggcatggcg    60
aatgggac                                                             68

<210> SEQ ID NO 6
<211> LENGTH: 28
<212> TYPE: DNA
<213> ORGANISM: Artificial Sequence
<220> FEATURE:
<223> OTHER INFORMATION: MCS sequence 2

<400> SEQUENCE: 6
gaattctgca gaggcctgca tgcaagct                                       28

<210> SEQ ID NO 7
<211> LENGTH: 227
<212> TYPE: DNA
<213> ORGANISM: Artificial Sequence
<220> FEATURE:
<223> OTHER INFORMATION: bGH polyA terminator

<400> SEQUENCE: 7
cgactgtgcc ttctagttgc cagccatctg ttgtttgccc ctcccccgtg ccttccttga    60
ccctggaagg tgccactccc actgtccttt cctaataaaa tgaggaaatt gcatcgcatt   120
gtctgagtag gtgtcattct attctggggg gtggggtggg gcaggacagc aaggggagg   180 attgggaaga caatagcagg catgctgggg atgcggtggg ctctatg                 227

<210> SEQ ID NO 8
<211> LENGTH: 8543
<212> TYPE: DNA
<213> ORGANISM: Artificial Sequence
<220> FEATURE:
<223> OTHER INFORMATION: Nucleotide Sequence of HAV Expression Cassette

<400> SEQUENCE: 8
acattgatta ttgactagtt attaatagta atcaattacg gggtcattag ttcatagccc    60
atatatggag ttccgcgtta cataacttac ggtaaatggc ccgcctggct gaccgcccaa   120
cgacccccgc ccattgacgt caataatgac gtatgttccc atagtaacgc caatagggac   180
tttccattga cgtcaatggg tggagtattt acggtaaact gcccacttgg cagtacatca   240
agtgtatcat atgccaagta cgccccctat tgacgtcaat gacggtaaat ggcccgcctg   300
gcattatgcc cagtacatga ccttatggga ctttcctact tggcagtaca tctacgtatt   360
agtcatcgct attaccatgg tgatgcggtt ttggcagtac atcaatgggc gtggatagcg   420
gtttgactca cggggatttc caagtctcca ccccattgac gtcaatggga gtttgttttg   480
gcaccaaaat caacgggact ttccaaaatg tcgtaacaac tccgccccat tgacgcaaat   540

```
gggcggtagg cgtgtacggt gggaggtcta tataagcaga gctctctggc taactagaga   600
acccactgct tactggctta tcgaaattaa tacgactcac tatagggagc tctcgcgaat   660
gcatgatatc ggatcctcga gccttcttga actgatgagg ccgaaaggcc gaaaacccgg   720
tatcccgggt tcttcaagaa gggtctccgg gaatttccgg agtccctctt ggaagtccat   780
ggtgagggga cttgatacct caccgccgtt tgcctaggct ataggctaaa ttttcccttt   840
cccttttccc tttcctattc cctttgtttt gcttgtaaat attgatttgt aaatattgat   900
tcctgcaggt tcagggttct aaatctgtt tctctataag aacactcatt tcacgctttc    960
tgtcttcttt cttccagggc tctcccttg ccctaggctc tggccgttgc gcccggcggg    1020
gtcaactcca tgattagcat ggagctgtag gagtctaaat tggggacaca gatgtttgga   1080
acgtcacctt gcagtgttaa cttggctttc atgaatctct ttgatcttcc acaaggggta   1140
ggctacgggt gaaacctctt aggctaatac ttctatgaag agatgccttg atagggtaa    1200 cagcggcgga tattggtgag ttgttaagac aaaaaccatt caacgccgga ggactgactc   1260
tcatccagtg gatgcattga gtggattgac tgtcggggct gtctttaggc ttaattccag   1320
acctctctgt gcttggggca aacatcattt ggccttaaat gggattctgt gagaggggat   1380
ccctccattg ccagctggac tgttctttgg ggccttatgt ggtgtttgcc gctgaggtac   1440 tcagggggcat ttaggttttt cctcattctt aaataataat gaacatgtct agacaaggta   1500
ttttccagac tgttgggagt ggtcttgacc acatcctgtc tttggcagac attgaggaag   1560
agcaaatgat tcaatcagtt gataggactg cagtgactgg tgcttcttat tttacttctg   1620
tggatcaatc ttcagttcat acagctgagg ttggatcaca ccaggttgaa cctttgagaa   1680
cctctgttga taaacccggt tcaaagagga ctcagggaga gaaatttttc ttgattcatt   1740
ctgcagattg gcttactaca catgctcttt tccatgaagt tgcaaaattg gatgtggtga   1800
aattattata caatgagcag tttgctgttc aagggttgtt gagataccat acatatgcaa   1860
gatttggcat tgaaattcaa gttcagataa accctacacc tttccaacag gggggattga   1920
tctgtgctat ggttcctggt gaccagagct atggttctat agcatcattg actgtttatc   1980
ctcatggttt gttaaattgc aatattaaca atgtggttag aataaaggtt ccatttattt   2040
acacaagagg tgcttaccac tttaaagatc cacaataccc agtttgggaa ttgacaatta   2100
gagtttggtc agaattaaat attgggacag gaacttcagc ttatacttca ctcaatgttt   2160
tagctagatt tacagatttg gagttgcatg gattaactcc tctttctaca caaatgatga   2220
gaaatgaatt tagggtcagt actactgaga atgtggtgaa tctgtcaaat tatgaagatg   2280
caagagcaaa gatgtctttt gctttggatc aggaagattg gaaatctgat ccgtcccagg   2340
gtggtgggat caaaaattact cattttacta cttggacatc tattccaact ttggctgctc   2400
agtttccatt taatgcttca gactcagttg gtcaacaaat taaagttatt ccagttgacc   2460
catatttttt ccaaatgaca aataaaaatc ctgaccaaaa atgtataact gctttggctt   2520
ctatttgtca gatgttttgt ttttggagag gagatcttgt ctttgatttt caagtttttc   2580
ccaccaaata tcattcaggt agattactgt tttgttttgt tcctggcaat gagctaatag   2640
atgtttctgg aatcacatta aagcaagcaa ctactgctcc ttgtgcagta atggatatta   2700
caggagtgca gtcaactttg agatttcgtg ttccctggat ttctgacact ccttacagag   2760
tgaacaggta tacaaagtca gcacatcaga aaggtgagta cactgccatt gggaagctta   2820
ttgtgtattg ttataacaga ttgacctctc cttctaacgt tgcttcccat gtcagagtga   2880
atgtttatct ttcagcaatt aacttggaat gttttgctcc tctttatcat gctatggatg   2940
```

```
ttactacaca agttggagat gattctggag gtttttcaac aacagtttct acagaacaga   3000
atgttccaga tccccaagtt ggtataacaa ccatgaaaga tttgaaagga aaagctaaca   3060
gagggaaaat ggatgtttca ggagtacaag cacctgtggg agctatcaca acaattgagg   3120
atccagtttt agcaaagaaa gtacctgaga catttcctga attgaaacct ggagaatcca   3180
gacatacatc agatcatatg tccatctaca agtttatggg aaggtctcat ttcttgtgca   3240
cttttacatt caattcaaat aataaagagt acacatttcc tataaccttg tcttcaacct   3300
ctaatcctcc tcatggtttg ccatcaacac tgaggtggtt tttcaacttg tttcagttgt   3360
atagagggcc tttagatctg acaattatta ttacaggagc aactgatgta gatggcatgg   3420
cctggtttac tccagtaggt cttgccgttg atactccttg ggtagagaag gagtcagctt   3480
tgtctattga ctacaaaact gctcttggag ctgtcagatt taacacaagg agaacaggga   3540
acattcagat tagattacca tggtattctt atttatatgc tgtgtctgga gcactggatg   3600
gtttgggtga caagacagat tctacatttg gattggtttc tattcagatt gcaaattaca   3660
atcattctga tgaatacttg tcttttagtt gttatttgtc tgtcacagaa caatcagagt   3720
tttattttcc cagagctcca ttgaactcaa atgccatgtt acccactgaa tcaatgatga   3780
gcagaattgc agctggagac ttggagtcat cagtggatga tcctagatca gaggaagata   3840
aaagatttga gagtcatata gaatgcagga agccatataa agaactgaga ttagaagttg   3900
ggaaacaaag actcaagtat gctcaggaag aattgtcaaa tgaagtactt ccacccccta   3960
ggaaaatgaa gggactgttt tcacaagcca atatttctct tttttatact gaggagcatg   4020
aaatgatgaa gttttcctgg agaggtgtga ctgctgatac tagagcttta aggaggtttg   4080
gattctcttt ggccgcaggc agaagtgtgt ggactcttga aatggatgct ggggttctta   4140
ctgggagact gattagattg aatgatgaga aatggacaga aatgaaggat gacaagattg   4200
tttcattgat tgaaaagttt acaagtaaca aatattggtc caaagtgaat ttcccacatg   4260
ggatgttgga tcttgaagaa attgctgcca attctaagga ttttcctaac atgtctgaaa   4320
cggatttgtg tttcttgctg cattggttaa atccaaagaa aattaattta gcagatagaa   4380
tgcttggatt gtctggagtt caggaaatta aagaacaagg tgttggatta atagcagagt   4440
gtagaacttt cttacattct attgctggaa ctttaaaatc tatgatgttt ggatttcatc   4500
attctgtgac tgttgaaatt ataaacactg tgctctgttt tgttaagagt ggaattttgc   4560
tttatgtaat acaacaattg aatcaggatg aacattctca cataattggt ctgttgagag   4620
tcttgaatta tgtagatatt ggttgttcag ttatttcatg tggcaaagtt ttttccaaaa   4680
tgctggaaac agtctttaat tggcaaatgg actccagaat gatggagtta aggactcaga   4740
gttttttcca ctggttaaga gatatttgtt ctgggatcac cattttaaa aacttcaagg   4800 atggaatttg ttggctttat acaaaattaa aggactttta tgaagtgaat tatggcaaga   4860
agaaggacat tttaaatatt cttaaagata accaacaaaa aatagagaaa gccattgagg   4920
aagccgataa attttgcatt ttgcaaatcc aagatgtgga aaaatctgaa cagtatcaga   4980
aaggggttga cttgatacaa aaaattgagaa ctgtttattc aatggctcag gttgatccaa   5040
atttaatggt tcatttgtca cctttgagag attgtatagc aagagttcat cagaaactta   5100
aaaaccttgg atttataaat caggcaatgg taacgagatg tgagccagtt gtttgttatt   5160
tacatggcaa aagagggga ggaaagagct aacatcaat tgcattggca accaaaattt   5220
gtaaacatta tggtgttgag cctgaaaaga atatctatac taaacctgtg gcttcagatt   5280
```

-continued

```
actgggatgg atatagtgga caattagttt gcatcattga tgatattggc caaaacacaa      5340
cagatgagga ctggtcagat ttttgtcagt tagtgtcagg atgtccaatg agattaaaca      5400
tggcctctct tgaggagaag ggtaggcatt tttcttctcc ttttataata gcaacttcaa      5460
attggtcaaa tccaagtcca aaaacagttt atgttaagga agcaattgac cgcagactcc      5520
atttcaaggt tgaagttaaa cctgcttcat ttttcaaaaa tcctcacaat gatatgttga      5580
atgttaattt agctaaaaca aatgatgcaa tcaaagatat gtcttgtgtt gatttgataa      5640
tggatggaca taatgtttca ttgatggatt tgctcagttc tttagtcatg acagttgata      5700
ttagaaaaca aaacatgact gaattcatgg agttgtggtc tcagggaatt tcagatgata      5760
atgatagtgc agtagctgag tttttccagt cttttccatc tggtgaacca tcgaactcta      5820
aattatctgg ctttttccaa tctgttacta atcacaagtg ggttgctgtg ggagctgcag      5880
ttggcattct tggagtgctc gttggaggat gggttgtgta taagcatttc tcccacaaag      5940
aggaagaacc aatcccagct gaaggggtat atcatggtgt aactaagccc aagcatgtga      6000
ttaaattaga tgcagatcca gtagaatctc agtcaacttt ggaaatagca ggactggtta      6060
ggaagaactt ggttcagttt ggagttggag agaagaatgg atgtgtgaga tgggttatga      6120
atgccttggg agtgaaagat gattggctgc ttgtgccttc ccatgcttat aaatttgaga      6180
aagattatga aatgatggag ttttatttta atagaggtgg aacttactat tcaatttcag      6240
ctggtaatgt tgttattcaa tctttggatg tgggattcca ggatgttgtt ctgatgaagg      6300
ttcctacaat tcctaagttt agagatatta ctgagcattt tattaagaaa ggggatgtgc      6360
ctagagcttt gaatcgcctg gcaacattag tgacaactgt aaatggaacc cctatgttaa      6420
tttctgaggg cccactaaag atggaagaga aagctactta tgttcataag aaaaatgatg      6480
gtacaacagt tgatttaact gtggatcagg catggagagg aaaaggcgaa ggtcttcctg      6540
gaatgtgtgg tggggccttg gtttcatcga atcaatctat acagaatgca atcttgggca      6600
tccatgttgc tggaggaaat tcaattcttg ttgcaaaatt ggttactcaa gaaatgttcc      6660
aaaatattga taagaaaatt gaaagtcaga gaattatgaa agtggagttt actcagtgtt      6720
caatgaatgt ggtctccaaa acgctttta gaaagagtcc catttatcat cacattgata      6780
aaaccatgat taattttcct gcagctatgc ccttttctaa agctgaaatt gatccaatgg      6840
ctgtgatgtt atctaagtat tcattaccta ttgtagaaga accagagggt tataaagagg      6900
cttcaatttt ttatcaaaat aaaatagtgg gtaagactca gttagttgat gattttctag      6960
atcttgatat ggccattaca ggggcccag gaattgatgc tatcaacatg gattcatctc      7020
ctggatttcc ttatgtccag gagaagttga ccaaaagaga tttaatttgg ttggatgaaa      7080
atggtttatt gctgggagtt catccaagat tggctcagag aatcttattc aatactgtca      7140
tgatggaaaa ttgttctgat ttggatgttg tttttacaac ctgtccaaaa gatgaattga      7200
ggccattaga gaaagtgttg gaatcaaaaa caagagctat tgatgcttgt cctctggatt      7260
acacaatttt gtgccgaatg tattgggtc cagctattag ttattttcat ttgaatccag      7320
gtttccatac aggtgttgct attggcatag atcctgataa acagtgggat gaactattta      7380
aaacaatgat aagattcgga gatgttggtc ttgatttaga tttctctgct tttgatgcta      7440
gtcttagtcc atttatgatt agagaagcag gtagaatcat gagtgaacta tctggaactc      7500
catcccattt tggcacagct cttatcaata ctatcattta ttccaagcat ttgctgtata      7560
actgttgtta ccatgtctgt ggttcaatgc cctctgggtc tccttgtaca gctttgctaa      7620
attcaattat taataatgtc aatttgtatt atgtgttttc taagatattt ggaaagtctc      7680
```

-continued

```
cagttttctt ttgtcaggct ttgaagattc tctgttatgg agatgatgtt ttaatagttt    7740
tctctcgaga tgttcagatt gataatcttg atttgattgg acaaaaaatt gtagatgagt    7800
ttaagaaact tggcatgaca gctacttctg ctgacaagaa tgtacctcag ctgaaaccag    7860
tttcggaatt gacttttctc aaaagatctt tcaatttggt agaggataga attagacctg    7920
caatttcgga aaaaacaatt tggtctttaa tagcatggca gagaagtaac gctgagtttg    7980
agcagaactt agaaaatgct cagtggtttg cttttatgca tggctatgag ttttatcaga    8040
aattctatta ttttgttcag tcctgtttgg agaaagagat gatagaatac agacttaaat    8100
cttatgattg gtggagaatg agatttttatg accagtgttt catttgtgac ctttcatgat    8160
ttgtttaaat gaactttctt aaaatttctg aggtttgttt atttctttta tcagtaaatg    8220
gccggcatgg tcccagcctc ctcgctggcg ccggctgggc aacatgcttc ggcatggcga    8280
atgggacgaa ttctgcagag gcctgcatgc aagcttcgac tgtgccttct agttgccagc    8340
catctgttgt ttgcccctcc cccgtgcctt ccttgaccct ggaaggtgcc actcccactg    8400
tcctttccta ataaaatgag gaaattgcat cgcattgtct gagtaggtgt cattctattc    8460
tggggggtgg ggtggggcag gacagcaagg gggaggattg ggaagacaat agcaggcatg    8520
ctggggatgc ggtgggctct atg                                           8543
```

HEPATITIS A VIRUS PREPARATION METHOD AND HEPATITIS A VIRUS PREPARED ACCORDING TO METHOD

TECHNICAL FIELD

This is a national phase application filed under 35 U.S.C. § 371 of PCT International Application No. PCT/KR2020/018703, filed on Dec. 18, 2020, entitled "HEPATITIS A VIRUS PREPARATION METHOD AND HEPATITIS A VIRUS PREPARED ACCORDING TO THE METHOD", which claims the priority of to, and benefit of, Korean Patent Application No. 10-2019-0171279, filed on Dec. 19, 2019, which are incorporated herein by reference in their entireties.

The present invention relates to a production method of hepatitis A virus and hepatitis A virus produced according to the method, and more specifically, to a preparation method of hepatitis A virus and hepatitis A virus prepared according to the method, the method comprising infecting a host cell with a virus obtained by transfecting the host cell with a vector inserted with an expression cassette comprising a hepatitis A virus gene for preparing the hepatitis A virus, and subculturing the same.

INCORPORATION-BY-REFERENCE OF MATERIAL SUBMITTED ELECTRONICALLY

A Sequence Listing conforming to the rules of WIPO Standard ST.25 is hereby incorporated by reference. Said Sequence Listing has been filed as an electronic document in ASCII format. The electronic document, created on Dec. 16, 2022, is entitled "11239-012US1_ST25.txt", and is 24,576 bytes in size.

BACKGROUND ART

Hepatitis A is the most important cause of over 70% of acute viral hepatitis in Korea. Hepatitis A virus (HAV) belongs to Picomaviridae and has a size of about 27 nm without an envelope, and has single-stranded RNA as a nucleic acid. After an average incubation period of 28 days, the HAV causes acute liver disease characterized by clinical symptoms such as fever, anorexia, nausea and vomiting, abdominal pain, dark urine, and jaundice (SM Lemon et al. J. Hepatol, 68 (1): 167-184 (2018); Totsuka and Moritsugu, Intervirology, 42:63-68 (1999)). According to a survey over the last 10 years, hepatitis A patients are increasing in the western United States, the Middle East, and some Asian regions, and worrying about the global spread of hepatitis A disease. Even in Korea, the number of people infected with hepatitis A is starting to increase rapidly among young people in their 10s and 20s who do not have immunity (Nwachuku and Gerba, Rev. Environ. Contam. Toxicol. 186:1-56 (2006); Kim and Lee, Intervirology, 53 (1): 10-14 (2010); Korea Centers for Disease Control and Prevention (KCDC) Infectious Diseases Portal Legal Infectious Disease Statistics by Disease-Hepatitis A). In particular, in the case of learning-age adolescents or test takers, hepatitis A virus infection causes personal and economic damage due to hospitalization and treatment. In the United States, it has been known that the direct and indirect cost of each hepatitis A patient is $2,500 for adults and about $1,500 for those under the age of 18, and medical expenses due to hepatitis A are more than 300 million dollars per year (World Health Organization, 1999).

The main transmission route of hepatitis A is the fecal-oral route, and hepatitis A is transmitted through contaminated food or drinking water. Advisory committee on immunization practices (ACIP) has recommended vaccination in outbound travelers to areas endemic to hepatitis A virus and workers in the corresponding areas, men who have sex with men (MSM), patients with hepatitis B, patients with chronic hepatic disease and chronic renal failure, and a children group living in areas with high incidence of hepatitis A (Nelson N P, Weng M K, Hofmeister M G, et al. Prevention of Hepatitis A Virus Infection in the United States: Recommendations of the Advisory Committee on Immunization Practices, 2020. MMWR Recomm Rep 2020; 69 (No. RR-5): 1-38. dx_doi_org/10.15585/mmwr.rr6905a1).

In order to prepare a hepatitis A vaccine, the preparation of hepatitis A virus (HAV) is necessarily accompanied, but hepatitis A virus has a very slow replication rate (Cromeans et al. J. Gen. Virol. 70:2051-2062 (1989)). Viruses that normally infect humans can be isolated and replicated if incubated for as short as 2 to 3 days or as long as 7 days, but in the case of hepatitis A virus, the virus can be obtained by culturing for about a month in short. The period equivalent to one month is also limited to a case where the virus is well adapted to incubated cells. Cell lines (e.g., Primary AGMK cell, FRhK-4, BS-C-1) with high sensitivity to hepatitis A virus used for amplification of hepatitis A virus are not suitable as cells for producing the vaccine. These cell lines have not been validated for cell line characterization and stability suitable to be used as a cell line for human vaccine production. In particular, the exemplary cells have been established as cell lines enabling in vitro culture in flasks, etc., but are classified as materials derived from *Macaca mulatta* and *Cercopithecus aethiops* belonging to the Cercopithecidae family, which are internationally endangered species restricted by the CITES, and thus it is difficult to be imported into Korea from ATCC (US), which distributes and sells cell lines commercially.

In order to be isolated from human fecal samples and produced in high yield in virus-producing cell lines, about 50 subcultures of virus infection are required to adapt HAV to the virus-producing cell lines. For example, in the case of a master seed virus (HAV 4380 or MRC5/9, Master seed) of Commercial Vaccine HAVRIX®, human-derived wt HM-175 (human stool suspension) is subjected to 32 passages in primary AGMK (African green monkey) cells to confirm a virus adapted to cell culture. Then, the corresponding virus (P-32 AGMK cell-adapted) is incubated to passage 37 in a MRC-5 cell line and isolated into virus clones (clone 25-4-21), and the clones are incubated once again in the MRC-5 (passage 38). Thereafter, a virus of passage 41, which was additionally passaged through virus infection in MRC-5 cells three times, was used as a master seed stock, which was specified as HAV 4380 (U.S. Pat. No. 6,423,318B1).

A hepatitis A vaccine is subject to mandatory vaccinations designated by the government, but is frequently in short supply during HAV epidemics. HAVRIX® of GlaxoSmithKline (GSK), Vaqta of Merck & Co., Inc., and the like, hepatitis A vaccines most frequently used around the world, were sold out in Korea, where hepatitis A was prevalent in 2019 and then have suffered from great difficulties in supply and demand, such as supply stopped by the end of 2019. The same imbalance problem in the supply and demand of these vaccines occurred in 2017, but the supply and demand instability was not resolved even in 2019, when the sudden spread of hepatitis A occurred. Currently, hepatitis A vaccines are included in the 2020 national vaccination vaccine stockpile plan for the stabilization of vaccine supply and demand by the Ministry of Health and Welfare and attempts to solve the problem are ongoing. There is a reason for this supply and demand instability why there is currently no commercial vaccine developed with domestic technology for hepatitis A vaccine.

DISCLOSURE

Technical Problem

The present inventors repeated intensive research to solve the above-mentioned technical problems and develop a method capable of stably and rapidly producing hepatitis A virus, and as a result, found a method for obtaining a virus by shortening about 50 times subculturing steps to only 6 times and an optimal gene expression cassette combination expressed with higher yield in virus-producing cell lines. Then, the present inventors found that a virus obtained by infecting a host cell with an expression vector comprising genetic and functional sites of hepatitis A virus was replicated at an astonishingly fast rate through repeated subculturing to produce hepatitis A virus rapidly and stably and then completed the present invention.

Therefore, an object of the present invention is to provide a hepatitis A virus gene defined by SEQ ID NO: 1.

Another object of the present invention is to provide an expression cassette for preparing hepatitis A virus comprising a hepatitis A virus gene of SEQ ID NO: 1, Yet another object of the present invention is to provide a vector for preparing hepatitis A virus comprising the expression cassette.

Yet another object of the present invention is to provide hepatitis A virus prepared with the vector.

Yet another object of the present invention is to provide a preparation method of hepatitis A virus for preparing a vaccine comprising steps of: (a) transfecting a host cell with a vector inserted with an expression cassette for preparing hepatitis A virus comprising a hepatitis A virus gene of SEQ ID NO: 1; (b) obtaining a virus from the host cell; (c) infecting the host cell with the obtained virus and subculturing the infected host cell; and (d) obtaining a virus from the host cell.

Another object of the present invention is to provide hepatitis virus prepared according to the method.

Another object of the present invention is to provide a hepatitis A vaccine composition comprising the hepatitis virus as an active ingredient.

Another object of the present invention is to provide a hepatitis A vaccine composition consisting of the hepatitis virus.

Another object of the present invention is to provide a hepatitis A vaccine composition essentially consisting of the hepatitis virus.

Another object of the present invention is to provide a kit comprising the vaccine composition.

Another object of the present invention is to provide a prefilled syringe filled with the vaccine composition.

Another object of the present invention is to provide use of the hepatitis virus for preparing a hepatitis A vaccine.

Another object of the present invention is to provide use of preventing hepatitis A of the vaccine composition comprising the hepatitis virus as an active ingredient.

Another object of the present invention is to provide a method for preventing hepatitis A comprising administering an effective dose of the vaccine composition comprising the hepatitis virus as an active ingredient to a subject in need thereof.

Technical Solution

In order to achieve the object of the present invention, the present invention provides a hepatitis A virus gene defined by SEQ ID NO: 1.

In order to achieve another object of the present invention, the present invention provides an expression cassette for preparing hepatitis A virus comprising a hepatitis A virus gene of SEQ ID NO: 1.

In order to achieve another object of the present invention, the present invention provides an expression vector for preparing hepatitis A virus comprising the expression cassette.

In order to achieve another object of the present invention, the present invention provides hepatitis A virus prepared with the vector.

In order to achieve another object of the present invention, the present invention provides a preparation method of hepatitis A virus for preparing a vaccine comprising steps of: (a) transfecting a host cell with a vector inserted with an expression cassette for preparing hepatitis A virus comprising a hepatitis A virus gene of SEQ ID NO: 1; (b) obtaining a virus from the host cell; (c) infecting the host cell with the obtained virus and subculturing the infected host cell; and (d) obtaining a virus from the host cell.

In order to achieve another object of the present invention, the present invention provides hepatitis virus prepared according to the method.

In order to achieve another object of the present invention, the present invention provides a hepatitis A vaccine composition comprising the hepatitis virus as an active ingredient.

In addition, the present invention provides a hepatitis A vaccine composition consisting of the hepatitis virus.

In addition, the present invention provides a hepatitis A vaccine composition essentially consisting of the hepatitis virus.

In order to achieve another object of the present invention, the present invention provides a kit comprising the vaccine composition.

In order to achieve another object of the present invention, the present invention provides a prefilled syringe filled with the vaccine composition.

In order to achieve another object of the present invention, the present invention provides use of the hepatitis virus for preparing a hepatitis A vaccine.

In order to achieve another object of the present invention, the present invention provides use of preventing hepatitis A of a vaccine composition comprising the hepatitis virus as an active ingredient.

In order to achieve another object of the present invention, the present invention provides a method for preventing hepatitis A comprising administering an effective dose of the vaccine composition comprising the hepatitis virus as an active ingredient to a subject in need thereof.

Hereinafter, the present invention will be described in detail.

The present invention provides a hepatitis A virus gene defined by SEQ ID NO:

In addition, the present invention provides an expression cassette for preparing hepatitis A virus comprising a hepatitis A virus gene of SEQ ID NO: 1.

The hepatitis A virus gene of SEQ ID NO: 1 provided by the present invention includes A2876T and A3891T point mutations as compared with a gene of a commercial A type virus line (ATCC VR-1402) and is characterized to be suitable for high yield and fast subculturing.

In particular, position 3891 is a major mutation in which an amino acid is changed from MET to LEU. A recombinant nucleotide sequence of the present invention was completed by giving a mutation to a major site capable of facilitating subculturing and increasing the yield.

According to an aspect of the present invention, it was confirmed that compared with commercially available wild-type hepatitis A virus as illustrated in FIGS. 8 and 11, the productivity of hepatitis A virus of the gene defined by SEQ ID NO: 1 according to the present invention was more excellent.

In the related art, in order to obtain hepatitis A virus, at least 47 times subculturing needs to be performed (FIG. 4), and there was a disadvantage that it is cumbersome, it takes a long time, and it is expensive (T. Cromeans et al., J Medical Virology 22:45-56, 1987). Typically, it takes about a month for one subculturing of HAV, and it takes several tens of months to obtain hepatitis A virus for vaccine preparation from human feces according to the related art. In the present invention, there is a technical feature that a hepatitis A virus gene of SEQ ID NO: 1 having the genetic mutation and an expression cassette comprising the same are used to reduce the production period of hepatitis A virus to 4 to 5 months.

In the present invention, the 'expression cassette' refers to a unit cassette capable of expressing a target protein operably linked to the downstream of the signal peptide to be secreted and produced by including a promoter, a nucleotide sequence encoding a signal peptide, and a gene encoding a target protein. Various factors capable of helping the efficient production of the target protein may be included inside or outside such an expression cassette.

In the present invention, the 'gene' is used broadly to refer to any segment of a polynucleotide that is associated with a biological function. Accordingly, the gene or polynucleotide includes intron and exon as in a genomic sequence, or only a coding sequence as in cDNA, such as an open reading that starts from a start codon (methionine codon) and ends to a stop signal (stop codon). The gene or polynucleotide may also include also sites that regulate their expression, such as transcription initiation, translation, and transcription termination. Accordingly, the gene or polynucleotide includes a promoter and a ribosome binding site (generally, these regulatory elements are usually located at approximately 60 to 250 nucleotides upstream of a start codon of the coding sequence or gene), and a transcription terminator (generally, the terminator is located within approximately 50 nucleotides downstream of the stop codon of the coding sequence or gene). The gene or polynucleotide also refers to a nucleic acid fragment that expresses mRNA or functional RNA, or encodes a specific protein, and comprises a regulatory sequence.

It may be apparent to those skilled in the art that the expression cassette provided by the present invention may include a nucleotide sequence encoding a polypeptide having substantially the same biological property such as antigenicity or immunogenicity of a virus while having at least 80% or more, preferably 90% or more, more preferably 95% or more sequence homology to the nucleotide sequence of the hepatitis A virus gene of SEQ ID NO: 1.

According to an aspect of the present invention, the expression cassette may include a promoter, a hammerhead (HH) ribozyme, and a hepatitis delta virus (HDV) ribozyme.

Preferably, the expression cassette comprises a CMV promoter, a T7 promoter, a multiple cloning site (MCS), and an HH ribozyme site in sequence at a 5' end of the hepatitis A virus gene, and may comprise a hepatitis delta virus ribozyme, an MCS, and a poly A tail in sequence in a 3' end direction of the hepatitis A virus gene.

According to a preferred embodiment of the present invention, the CMV/T7 promoter may be defined by SEQ ID NO: 2, the MCS sequence may be defined by SEQ ID NO: 3 or 6, the HH ribozyme may be defined by SEQ ID NO: 4, the HDV ribozyme may be defined by SEQ ID NO: 5, and the poly A tail may be defined by SEQ ID NO: 7. In one embodiment of the present invention, a CMV promoter site and a T7 promoter site capable of in-vitro transcription by T7 RNA polymerase were inserted into an expression cassette for gene expression (SEQ ID NO: 2). The MCS was disposed behind the promoter at the 5' end of the gene (SEQ ID NO: 3) and before the poly A tail sequence (SEQ ID NO: 6) so as to use a restriction enzyme. The expression cassette was designed so that as a catalytic RNA cleavage structure with a self-cleavage function, HH ribozyme (SEQ ID NO: 4) and HDV ribozyme (SEQ ID NO: 5) sites are positioned on both sides of a UTR-HAV polyprotein-UTR site, which is a HAV sequence site, and may be isolated (processed) only from an HAV mRNA structure to be targeted.

According to a preferred embodiment of the present invention, the expression cassette may include a nucleotide sequence of SEQ ID NO: 8.

In addition, the present invention provides a vector for preparing hepatitis A virus comprising the expression cassette.

In the present invention, the "vector" is a vector capable of expressing a target protein in a suitable host cell and refers to a gene construct including a required regulatory element which is operably linked so that a gene insertion is expressed. In the present invention, the "operably linked" means that a nucleic acid sequence encoding a target protein is functionally linked to a nucleic acid expression regulatory sequence to perform a general function. The operative linkage with the vector may be prepared using a genetic recombination technique well-known in the art to which the present invention pertains, and site-specific DNA cleavage and linkage may be easily performed using enzymes generally known in the art to which the present invention pertains.

A suitable vector that may be used in the present invention may include not only an expression regulatory element such as a promoter, a start codon, a stop codon, a polyadenylation signal, a ribozyme and an enhancer, but also a signal sequence for membrane targeting or secretion in addition to the hepatitis A gene of SEQ ID NO: 1.

The start codon and the stop codon are generally considered as a part of the nucleotide sequence encoding an immunogenic target protein, and need to exhibit actions in the host cell when the gene construct is administered, and needs to be in frame with the coding sequence. A general promoter may be constitutive or inductive. The promoter includes human elongation factor-1 alpha (EF-1α), simian virus 40 (SV40), mouse mammary tumor virus (MMTV) promoter, cytomegalovirus (CMV), a β-actin promoter, a T7 promoter, and a T3 promoter, but is not limited thereto.

When the vector is a replicable expression vector, the vector may include a replication origin, which is a specific nucleic acid sequence from which replication is initiated. As the recombinant expression vector, various types of vectors such as plasmid, virus, and cosmid may be used. The type of recombinant vector is not particularly limited as long as the recombinant vector functions to express a desired gene and produce a desired protein in various host cells of eukaryotic cells, but a vector capable of mass-producing a promoter exhibiting strong activity and a foreign protein in a form similar to that of a natural state while retaining a strong expression power is preferable.

An eukaryotic expression vector into which the expression cassette for preparing hepatitis A virus including the hepatitis A gene of SEQ ID NO: 1 may be inserted is known in the art. Non-limiting examples thereof include a pUC57 vector, a pcDNA3.1 vector, a pVAXI vector (Life Technology, Cergy-pontoise, France), and pBudCE4.1 (Life Technology), and vectors disclosed or mentioned herein or known to those skilled in the art may be used to prepare the expression vector of the present invention. Preferably, the pUC57 vector may be used.

According to another preferred embodiment of the present invention, the vector may show a cleavage map of the HAV virus gene illustrated in FIG. 2 and factors involved in gene expression for generating the virus.

The present invention provides a preparation method of hepatitis A virus for preparing a vaccine comprising steps of: (a) transfecting a host cell with a vector inserted with an expression cassette including a hepatitis A virus gene of SEQ ID NO: 1 for preparing a hepatitis A virus; (b) obtaining a virus from the host cell; (c) infecting the host cell with the obtained virus and subculturing the infected host cell; and (d) obtaining a virus from the host cell.

(a) Transfecting a host cell with a vector inserted with an expression cassette including a hepatitis A virus gene of SEQ ID NO: 1 for preparing a hepatitis A virus;

The 'expression cassette' and the 'vector' may be applied in the same manner as those described above.

In the present invention, the 'host cell' refers to a eukaryotic cell that has been genetically altered or may be genetically altered by administration of an exogenous polynucleotide, such as a recombinant plasmid or vector. When referring to the genetically altered cell, the term includes both an initially altered cell and its progeny. The polynucleotide or the expression cassette comprising the hepatitis A virus gene sequence of SEQ ID NO: 1 may be inserted into a cloning vector and an expression vector, and then the vectors may be injected into a suitable host cell for replication and amplification.

The type of host cell into which the vector is injected in step (a) of the present invention is not particularly limited, but may be a cell derived from a natural host (e.g., chimpanzee, monkey, human, etc.) of HAV or a cell for vaccine production. The 'cell for vaccine production' may also be expressed even as a cell substrate and may be defined as having the ability to produce medicines among cell lines derived from humans or animals as raw materials for preparing biomedicines or cell culture drugs.

In particular, in the present invention, the host cell is preferably used for producing biological drugs in the art because safety has been proven as a cell for human vaccine production. A detailed description of cells that the safety has been proven as the cell for human vaccine production may refer to Jordan and Sandig, Viruses, 6:1672-1700 (2014); WHO Technical Report Series, No. 978, Annex 3, and all contents of these documents may be referred to the contents of the present invention.

According to one aspect of the present invention, the cell for vaccine production may be selected from the group consisting of Vero, MA104, WI-38, CHO, MDCK, Hi5, CEF, S9, Human Embryonic Lung Fibroblast (e.g., MRC-5, etc.), PER.C6, BHK-21, CHO-K1 and serum-free adaptive cells thereof. Preferably, the cell for vaccine production may be selected from MA104, Vero, or serum-free adaptive cells thereof. More preferably, the cell may be a SF-Vero cell.

According to one aspect of the present invention, the culturing of the host cell may be performed as follows: MA104 and Vero cell lines use an EMEM (2% FBS-EMEM) medium containing 2% FBS, and an SF-Vero cell line is exchanged with 2 mL of a serum-free EMEM medium (SF-EMEM) and may be incubated for 2 to 4 weeks (preferably 3 weeks) at 30 to 40° C. (preferably at 35° C.), in 3 to 7% (preferably 5%) $CO_2$ incubator.

When a corresponding temperature range, a carbon dioxide concentration range, and the number of incubation days are insufficient or exceeded, an appropriate number of cell lines may not be generated, and appropriate conditions for transfection of the HAV gene construct may not be formed.

Cell adaptation for incubation in the serum-free medium may be easily achieved by those skilled in the art by gradually subculturing the cell in a medium in which the amount of serum is reduced until the cells may successfully survive and proliferate in the serum-free medium, so that a serum-free adapted cell line of each cell line may be easily obtained by those skilled in the art.

In the present invention, the vector may be injected into a host cell by any method known in the art. The vector inserted with the expressing cassette for preparing the hepatitis A virus including the hepatitis A virus gene of SEQ ID NO: 1 may be injected into the host cell by a plurality of suitable means including endocytosis, transfection, electroporation, transfection using calcium chloride, rubidium chloride, calcium phosphate, DEAE-dextran, or other components; microparticle projection; lipofection; and viral vector injection (e.g., retroviral vector).

(b) Obtaining a virus from the host cell;

After step (a), the host cell transfected with the vector is incubated in a nutrient medium to obtain hepatitis A virus to be used as a seed, and tolerated medium and incubation conditions to be used at this time may be appropriately selected and used depending on the host cell. During incubation, conditions such as a temperature, a pH of the medium, and an incubation time may be appropriately adjusted to be suitable for cell growth and virus production. As such, the virus produced or secreted in the host cell may be recovered from a supernatant or a cell lysate of the culture medium, and can be isolated and purified by conventional protein and virus isolation techniques.

The virus obtained in step (b) is then infected in the host cell and used as a seed for amplification, and in one embodiment of the present invention, the virus was named passage 0 (P0) virus.

(c) Infecting the host cell with the obtained virus and subculturing the infected host cell;

In step (c) of the present invention, the P0 virus obtained in step (b) is infected in the host cell and subcultured repeatedly to generate a virus that can be adapted to the host cell and amplified at a high speed.

According to one embodiment of the present invention, when the infection passage proceeds, the host cells MA104 and Vero may be prepared at $1 \times 10^5$ to $1 \times 10^7$ cells/5 mL, and the SF-Vero cells are prepared at $5 \times 10^5$ to $5 \times 10^7$ cells/5 m. When the host cells are prepared at a lower concentration than the corresponding concentration, it may be difficult to obtain a satisfactory titer, and when the host cell is prepared at a higher concentration than the corresponding concentration, the infection of the host cell may not occur evenly, so that it may not be economical.

According to one embodiment of the present invention, the host cell may be incubated at 30 to 40° C. (preferably 35° C.) in a 3 to 7% (preferably 5%) $CO_2$ incubator for 2 to 4 weeks (preferably 3 weeks). When the corresponding temperature range, the carbon dioxide concentration range, and the number of incubation days are insufficient or exceeded, an appropriate number of cell lines may not be generated, and appropriate conditions for subculturing may not be formed.

According to an embodiment of the present invention, during a P1 infection passage, M104 and VERO cells were prepared at $5\times10^5$ to $5\times 10^7$ cells/30 mL, and the SF-Vero cells were prepared at $8\times10^5$ to $8\times10^7$ cells/30 mL, and the medium may be removed from the cells prepared just before infection and washed with 30 mL DPBS 1 to 3 times. The virus may not be obtained in optimal yield when the corresponding conditions are insufficient or exceeded.

According to an embodiment of the present invention, 1 to 10 mL of an infection medium may be used for P1 to P4 infection passages, and 20 to 50 mL of the infection medium may be used for P5 to P6 infection passages. The virus may not be obtained in optimal yield when the corresponding conditions are insufficient or exceeded.

In the present invention, the passage means to continuously maintain the passage of the virus-infected host cell even if the experimental confirmation of virus proliferation in culture, that is, a cytopathic effect or detection of the virus is not confirmed after the virus is infected in the host cell.

The host cell infected with the virus in step (c) is preferably to use the same as the host cell used to prepare the P0 virus in step (a).

According to one embodiment of the present invention, the subculturing may be specifically performed according to the following method. The host cell is treated and infected with the P0 virus and then incubated. After culturing, the host cell is crushed and centrifuged to remove cell debris and only the supernatant is obtained. The host cell infection is performed using the obtained supernatant passage 1 (P1).

The process of infecting the host cell infection—culturing the host cell—crushing the host cell—obtaining the supernatant is repeated at one cycle to perform the passage.

In the passage process of one cycle of the present invention, the culture of the host cell may be performed for preferably 5 days to 30 days, more preferably 10 days to 25 days, even more preferably 17 days to 21 days, and most preferably 19 days to 21 days.

In each subculturing process, the proliferation of the virus is performed in a medium composition in which the host cell is generally incubated. The host cell is incubated in a standard commercial culture medium such as a serum (e.g., 10% fetal bovine serum) supplemented medium or a serum-free medium, under a $CO_2$ concentration suitable to maintain a neutral buffered pH (e.g., pH between 7.0 and 7.2) and controlled humidity. Optionally, the medium may contain additional nutrients, such as L-glutamine, vitamins, sugars, amino acids, peptides, trace elements, sodium pyruvate, peptone, vitamins, sugars (e.g., glucose), and non-essential amino acids, and additional supplements promoting desirable growth properties (e.g., trypsin, β-mercaptoethanol, insulin, growth factors, amino acid complexes, etc.).

In some cases, for example, for the preparation of the virus, it is preferred to grow the host cell under serum-free conditions. The cell may be attach-incubated in a small scale, such as less than 25 mL of a medium, a culture tubes or a flask, or in a large flask (e.g., Cell Factory System) and may be incubated on a stirred large flask, a rotator bottle, and a microcarrier (e.g., Cytodex, GE Healthcare) in a reactor culture solution. Microcarrier beads are small spheres (diameter in the range of 50 to 100 μm) that provide a large surface area for adherent cell growth per volume of the cell culture. For example, in the case of commercial virus production such as vaccine production, it is often preferred to culture the cells in a bioreactor or fermenter. The bioreactor can be used in volumes from 1 L or less to more than 100 L, and for example, may also be used from an NBS bioreactor (New Brunswick Scientific, Edison, N. J.); Sartorius Stedim Biotech, Gottingen, Germany) or a scale-X bioreactor (scale-X single-use bioreactor system; Univercells Technologies, Belgium) to a commercial-scale bioreactor.

In the present invention, regardless of a culture volume, it is important to maintain the culture solution at a temperature of 35° C. or less to ensure effective preparation of hepatitis A virus. In general, it is preferred to use a controller, such as a thermostat, or other devices for sensing and maintaining the temperature of the cell culture system, so that the temperature does not exceed 35° C. during the virus replication period.

The process of maintaining cells in culture have been extensively reported and are known in the art. General protocols are known in the art, and changes in conditions during the cell culture process may be easily determined through routine experiments.

On the other hand, in the present invention, the subculturing may repeat 1 passage of 1 cycle described above 2 to 30 times, preferably 2 to 20 times, more preferably 4 to 20 times, even more preferably 4 to 15 times, and most preferably 4 to 10 times.

(b) Obtaining a Virus from the Host Cell

Step (d) of the present invention is a step of recovering the virus for vaccine production by repeating the step (c) to obtain the host cell and a culture medium thereof.

Preferably, in step (d), the virus may be obtained when a cytopathic effect appears in the host cell.

In the present invention, the cytopathic effect refers to all effects in cells caused by the infection of hepatitis A virus. The cytopathic effect includes plaque formation, cell granulation and fragmentation and cell detachment from supports (e.g., cell-virus culture flasks), cell shrinkage, cell aggregation, cell lysis, cell rounding denaturation, soughing, apoptosis induction, and the like, but is not limited thereto. The cytopathic effect may also be generally confirmed by observation with a microscope or with the naked eye.

Meanwhile, in step (d) of the present invention, after the virus is obtained from the cell culture solution and cells after the cytopathic effect appears in the host cell, additional subculturing is performed to obtain a desired amount of virus for each passage, and step (d) may also be performed by repeating the passage again.

In the present invention, the amount of virus refers to an amount of virus measured by virus titer (specifically, the content of a hepatitis A antigen), the size or shape of a plaque, the particle density, or other means known in the art.

According to an embodiment of the present invention, the cytopathic effect (CPE) started to be observed after passage 3 in the host cell repeatedly passaged according to the above-described method, and after passage 4 or 5, it was confirmed that the amount of virus released into the culture medium and the amount of virus in the cells are significantly increased. In addition, it was confirmed that the amount of virus released into the culture medium or the amount of virus in the cells was not decreased but maintained even if the passage was continued. As a representative example, virus particles were confirmed by transmission electron microscopy (TEM) in infection passage 3 in the SF-Vero cell line, and electron micrographs of the virus particles prepared in FIGS. 5A to 5C are shown.

Therefore, in the present invention, step (d) may be performed after performing the subculturing in step (c) at least twice, preferably three times or more, more preferably four or more times, but the present invention is not limited thereto. Even after the cytopathic effect is observed in the host cell, when it is desired to further amplify the amount of virus, the virus can be obtained at the time when the desired level of virus is obtained by repeatedly performing subculturing.

The method of the present invention may further include a virus purification step and a virus inactivation step in order to utilize the virus obtained after step (d) as a vaccine.

In the present invention, the purification may be performed through a main purification method or a main purification step, for example, chromatography, or a density gradient ultracentrifugation purification method. The chromatography may include resin ion exchange chromatography, hydrophobic interaction chromatography, mixed chromatography, membrane chromatography, or the like. In addition, ion exchange chromatography and size exclusion chromatography may be performed simultaneously, and ion exchange chromatography and multimodal chromatography may be performed simultaneously.

In the present invention, the inactivation step is performed for complete removal of viral infectivity, and in general, the inactivation step may be performed by a chemical or physical means. For chemical inactivation, the virus may be inactivated with an inactivation solution containing, for example, formaldehyde or beta-propiolactone at an appropriate concentration. A residual inactivating material may be neutralized later if necessary. The material inactivated with formaldehyde may be neutralized with a formaldehyde neutralizer containing, for example, sodium sulfite or sodium bisulfite, and may be exchanged to a phosphate buffer, a physiological saline, or a buffer that maintains virus safety through diafiltration.

In the present invention, the order of the purification and inactivation steps is not particularly limited, and the inactivation step after purification may be performed or the purification step after inactivation may be performed. Preferably, the purification step after inactivation may be performed.

The present invention provides hepatitis A virus prepared according to the method including steps (a) to (d).

The hepatitis A virus prepared according to the method of the present invention is very fast in amplification speed in a cell line that has been used industrially because safety as the vaccine production cell line has been secured or proven, or approved or certified as a biological drug production cell substrate by national health authorities, including WHO. In addition, the virus can be stably amplified even after a long-term subculturing is repeated in the host cell, and thus, the virus may be very usefully used for the production of a hepatitis A vaccine.

The present invention also provides a vaccine composition comprising the virus as an active ingredient.

In the present invention, the vaccine may be a live vaccine, an attenuated vaccine, or an inactivated vaccine.

The 'live vaccine' means a vaccine that contains a living viral active ingredient. The 'attenuation' refers to weakening the pathogenicity of a living virus by artificial or natural factors, and inducing immunity by stimulating only an immune system without causing a disease in the body. The attenuation of the virus may be achieved by performing virus particle heat treatment, UV light irradiation to the virus, high-order continuous subculturing in vitro, or continuous virus subculturing in incubated cells in an in vitro culture container such as a culture flask several times. The attenuation may also be achieved by making distinct genetic changes, for example, by specific deletion of viral sequences known to provide toxicity or insertion of sequences into a viral genome. The 'inactivated vaccine' is also called an inactivated vaccine, and is a vaccine containing a virus from which infectivity has been removed. Examples thereof include a whole virus vaccine and a split virus vaccine, which can be easily prepared by known methods.

The vaccine composition of the present invention may further include one, two, or three or more adjuvants in addition to the aforementioned virus. The term 'adjuvant' refers to a compound or mixture that enhances the immune response to an antigen. The adjuvant may act primarily as a delivery system, act primarily as an immune modulator, or have strong characteristics of both. A suitable adjuvant includes those suitable to be used in mammals, including humans.

The adjuvant suitable for increasing the effectiveness of the vaccine composition of the present invention includes the following materials, but is not limited thereto:

(1) aluminum salts (alum) (e.g., aluminum hydroxide, aluminum phosphate, aluminum sulfate, etc.);

(2) oil-in-water emulsion formulations (with or without other specific immune stimulating agents such as muramyl peptide or bacterial cell wall component);

(3) particles used with or generated from a saponin adjuvant such as Quil A or STIMULON™ QS-21 [Antigenics, Framingham, MA] (U.S. Pat. No. 5,057, 540);

(4) synthetic polynucleotides; and (5) cytokines such as interleukin, interferon, granulocyte macrophage colony stimulating factor, macrophage colony stimulating factor, tumor necrosis factor and the like.

In a specific embodiment, an aluminum-based adjuvant may be used. The aluminum salt adjuvant may be an alum precipitated vaccine or an alum-adsorbed vaccine. The aluminum salt includes alumina hydrate, aluminum oxide, aluminum trihydrate, aluminum phosphate gel, Superfos, amphogel, aluminum (III) hydroxide, aluminum phosphate adjuvant (APA), amorphous alumina, and the like, but is not limited thereto. The aluminum salt forms an antigen reservoir that releases an antigen slowly for 2 to 3 weeks to non-specifically activate macrophages, complements, and innate immune mechanisms.

In another specific embodiment, the vaccine composition disclosed the present invention may include a CpG oligonucleotide as an adjuvant. The CpG oligonucleotide refers to immunostimulatory CpG oligodeoxynucleotide (CpG ODN), and thus, the terms are used interchangeably unless otherwise indicated.

The adjuvant is appropriately selected according to the amount and valence of a conjugate in the composition, but when an aluminum-based adjuvant is used, the aluminum element may be added to be included in the composition in an amount of 0.01 mg/mL to 1.0 mg/mL based on the aluminum element. Preferably, the aluminum element in the composition may be contained in an amount of 0.1 mg/mL to 0.6 mg/mL, or 0.1 mg/mL to 0.4 mg/mL, and more preferably, the aluminum element in the composition may be contained in an amount of 0.15 mg/mL to 0.35 mg/mL.

As long as the vaccine composition of the present invention achieves its effect, the formulation providing the composition is not particularly limited.

The vaccine compositions of the present invention may be formulated in a liquid form (i.e., a solution or a suspension) or a lyophilized form. In one embodiment, the vaccine composition of the present invention is in a liquid form, preferably in an aqueous liquid form. When provided as the liquid formulation, the vaccine composition of the present invention is provided in a form in which the liquid formulation is packaged in a container (preferably, a syringe) to be administered directly without a separate vaccine composition reproduction process such as redispersion. Accordingly, the liquid formulation may be ideal for injection and reproducing a certain effect, unlike the composition of the lyophilized formulation which requires resuspension in an aqueous medium.

The formulation of the vaccine composition of the present invention may be performed using various methods known in the art. For example, the composition may be prepared by formulating the hepatitis A virus in a physiologically acceptable vehicle. Examples of the vehicle include water, buffered saline, polyols (e.g., glycerol, propylene glycol, and liquid polyethylene glycol), polysorbate 20 and a dextrose solution, but are not limited thereto.

The present invention provides a vaccine composition comprising the hepatitis A virus disclosed in the present invention and a pharmaceutically acceptable excipient, carrier, isotonic agent or diluent. The types of the excipient, carrier or diluent are known in the art to be used according to a route of administration of a pharmaceutical composition to be described below.

In one example, the pharmaceutically acceptable carrier used in the liquid formulation includes aqueous or non-aqueous solvents, suspensions, emulsions, and oils. Examples of the non-aqueous solvent include propylene glycol, polyethylene glycol, and ethyl oleate. The aqueous solvent includes water, an aqueous solution, an emulsion or suspension, a physiological saline, and a buffer solution. The pharmaceutical composition may be isotonic, hypotonic or hypertonic. However, the pharmaceutical composition administered by injection is preferably basically isotonic. Accordingly, isotonicity or hypertonicity may be advantageous for storage of the composition. When the pharmaceutical composition is hypertonic, the pharmaceutical composition may be diluted to be isotonic before administration. An isotonic agent may be an ionic isotonic agent or a non-ionic isotonic agent. The ionic isotonic agent includes sodium chloride, calcium chloride, potassium chloride, magnesium chloride, and the like, but is not limited thereto. The non-ionic isotonic agent includes sorbitol, glycerol, and the like, but is not limited thereto. Preferably, at least one pharmaceutically acceptable buffer is included. For example, when the pharmaceutical composition is an injection, the pharmaceutical composition is preferably composed of a buffer having buffering capacity at pH 5.0 to pH 9.0, for example, pH 6.0 to pH 8.0, and pH 6.8 to pH 7.5. The buffer may be selected from a buffer consisting of potassium phosphate, sodium monohydrogen phosphate, glutamate, carbonate, borate, lactate, citrate, histidine, glycine, triethanolamine, and the like.

The vaccine composition of the present disclosure may additionally include at least one selected from the group consisting of a buffering agent, a salt, a divalent cation, a surfactant (particularly, a non-ionic detergent), a cryoprotectant (e.g., sugar), an anti-oxidant (e.g., a chelating agent), a preservative and an anti-fungal agent.

The type of buffering agent is not particularly limited as long as the buffering agent is known in the art for use in a pharmaceutical composition, particularly a vaccine composition, but may use histidine, citrate, phosphate, succinate, or 4-(2-hydroxyethyl)-1-piperazineethanesulfonic acid (Hepes). These buffering agents may be used in the form of any compound, and for example, phosphate may be used in the form of sodium phosphate and potassium phosphate.

In one embodiment, the vaccine composition of the present invention comprises a salt. The salt type is not particularly limited as long as the salt is known in the art for use in the pharmaceutical composition, particularly the vaccine composition, but may be selected from the group consisting of magnesium chloride, potassium chloride, sodium chloride, borate chloride, and combinations thereof.

In one embodiment, the vaccine composition of the present invention comprises a surfactant. In one preferred embodiment, a non-ionic detergent is used. In one embodiment, the surfactant is selected from the group consisting of polysorbate 20 (Tween™ 20), polysorbate 40 (Tween™ 40), polysorbate 60 (Tween™ 60), polysorbate 65 (Twin™ 65), polysorbate 80 (Twin™ 80), polysorbate 85 (Twin™ 85), Triton™ N-101, Triton™ X-100, octoxynol 40, nonoxynol-9, triethanolamine, triethanolamine polypeptide oleate, polyoxyethylene-660 hydroxystearate (PEG-15, Solutol H 15), octylthioglucoside (OTG), octylglucoside (OG), nonylmaltoside (NM), lauryldimethylamine oxide (LDAO), dodecyl beta-D-maltoside (DDM) and poloxamer.

In the present invention, the 'each dose' is used in the same meaning as a 'unit dose or 'one dosage', and may be used interchangeably herein. Preferably, the unit dose may refer to a unit suitable as a unitary dosage for animals, preferably mammals, particularly a human, and each unit contains an antigenic material calculated to produce a preventing or immunizing effect for a disease desired by those skilled in the art (in particular, without the risk of serious side effects at the same time). In a preferred embodiment, the vaccine composition provided in the present invention may be provided in the form of a unit dose.

The dose may use a suitable amount set by those skilled in the art according to the technical common knowledge in the field of pharmaceutical preparation, such as its administration means or route of administration, and for example, one dosage for injection may be 0.5 mL, 0.6 mL, 0.7 mL, 0.8 mL, 0.9 mL, or 1.0 mL, but is not limited thereto.

As a more convenient means for directly providing the user with the vaccine composition of the present invention described above, the present invention provides a container filled with any of the vaccine composition described above.

The type of the container is not particularly limited as long as the container is known in the art to be used for providing the pharmaceutical composition or the vaccine composition. In one embodiment, the container is selected from the group consisting of a prefilled syringe, a vial, a syringe, a sterile single use needle, a microneedle patch, an ampule, and a dosing cartridge.

A typical single injection dose of the vaccine composition of the present invention may be provided in a volume of 0.5 mL or 1.0 mL, more preferably 0.5 mL or 1.0 mL depending on an administration group.

Accordingly, the container or syringe as defined above may be provided in which the vaccine composition of the present invention is filled in a volume of the single injection dose. In one embodiment, the container or syringe may be provided to be filled with, for example, any one of the vaccine composition defined in the present invention in a volume of 0.5 mL or 1.0 mL.

The present invention also provides a kit comprising the vaccine composition of the present invention described above. Specific components of the kit may refer to a provision form known in the art according to the provision form of the composition. It is apparent that any container filled with the aforementioned vaccine composition is included in the kit.

In one example, the kit may provide one or more vials containing or not containing the vaccine composition of the present invention (a liquid formulation or a lyophilized formulation), one or more syringes containing or not containing the vaccine composition of the present invention, or a kit including all of the vials or the syringes.

In addition, when the vaccine composition of the present invention is provided in a liquid formulation, the vaccine material is contained in a prefilled syringe, and the material at this time becomes a material for patient administration. The vaccine composition may be administered to a patient by attaching a sterile injection needle to the inlet of the prefilled syringe.

The kit may also include package inserts to be provided to the user.

In the present invention, the kit may provide the vaccine composition in a dose for a single inoculation schedule, or may be provided in a dose for a multiple (split) inoculation schedule.

In one embodiment, the vaccine composition disclosed herein is for use as a drug (pharmaceutical composition). The vaccine composition disclosed in the present invention may be used as a pharmaceutical composition in various therapeutic or prophylactic methods for the prevention, treatment or improvement of bacterial infection, disease or condition in a subject. In particular, the vaccine composition disclosed in the present invention may be used for preventing, treating or improving the infection, disease or condition caused by hepatitis A virus in the subject.

Further, the present invention provides a vaccination method for preventing hepatitis A characterized by administering an effective amount of the vaccine composition of the present invention described above to an individual in need thereof.

In the present invention, the 'effective amount' refers to an amount exhibiting death of hepatitis A virus or the effect of improving, treating or preventing the infection, disease or condition related to hepatitis A virus when administered to the individual.

In one embodiment, the effective amount is an immunologically effective amount. The immunologically effective amount refers to an amount of an antigen or vaccine sufficient to cause either a cellular (T cell) or humoral (B cell or antibody) immune response, when measured by standard assays known to those skilled in the art. The level of an antigen as an immunogen, for example, a viral antigen or an antigen-specific antiserum or neutralizing antibody induced by the vaccine thereof is measured or may be measured by detecting cytokines secreted by t cells stimulated by the viral antigen. In addition, the protection level of the immune response may be measured by identifying a reduction in antigen-derived viral infection in an immunized individual or prevention of diseases resulting from infection.

In one embodiment, the effective amount is a prophylactically effective amount. In the present invention, the term 'prevention' refers to inhibiting the occurrence of a disorder or disease in an individual who has never been diagnosed with a disorder or disease, but is prone to such disorder or disease. Accordingly, as used herein, the term 'prophylactically effective amount' means an amount sufficient to achieve the pharmacological effect.

In a specific embodiment, the vaccine composition disclosed herein may be used to prevent hepatitis A in a subject. Accordingly, the present invention provides a method for preventing hepatitis A characterized by administering an effective amount of the vaccine composition of the present invention described above to an individual in need thereof.

In the present invention, the term 'individual' may be used interchangeably with a 'subject', and may be animals, preferably mammals, particularly including humans, such as cats, sheep, pigs, horses, cattle or dogs, etc., and may also be animal-derived cells, tissues, organs, or the like. The individual may be patients requiring the effects.

In one embodiment of the present invention, the immunodepressed individual disclosed herein is any human male or human female.

In the vaccine composition of the present invention, the route of administration is not particularly limited as long as the desired effect is achieved in the body, but the vaccine composition is administered through intramuscular, intraperitoneal, intradermal, subcutaneous, rectal, systemic or mucosal routes to be used to protect or treat humans susceptible to hepatitis A virus infection.

The vaccine composition of the present invention may be provided in a single dose or in multiple doses. In some cases, as little as one dose of the vaccine composition according to the present invention is required, but in some cases, for example, under conditions of greater immunodeficiency, a second, third or fourth dose may also be provided. Following the initial vaccination, one or several (multiple) additional immunizations may be performed for the subject at appropriate intervals.

The present invention also provides a kit comprising the vaccine composition.

The present invention also provides a prefilled syringe filled with the vaccine composition.

The kit and the prefilled syringe may include the HAV vaccine composition and the pharmaceutically acceptable carrier. In addition, the kit and the prefilled syringe may additionally include instructions for basic matters (precautions during administration, dosing cycle, storage temperature, expiration date, etc.) to be observed in order to prevent HAV infection.

The present invention provides use of the virus for preparing a hepatitis A vaccine.

The present invention provides use of preventing hepatitis A of a vaccine composition comprising the hepatitis virus as an active ingredient.

The present invention provides a method for preventing hepatitis A comprising administering an effective dose of the vaccine composition comprising the hepatitis virus as an active ingredient to an individual in need thereof.

The term "comprising" used herein is used in the same meaning as "including" or "characterized by", and does not exclude additional ingredients or steps of the method which are not specifically mentioned in the composition or the method according to the present invention. The term "consisting of" means excluding additional elements, steps or ingredients, etc., unless otherwise described. The term "essentially consisting of" means including materials or steps which do not substantially affect basic properties thereof in addition to the described materials or steps within the range of the composition or the method.

Advantageous Effects

According to the method for preparing the hepatitis A virus provided by the present invention, it is possible to prepare hepatitis A virus that is stably amplified within a short period to be very useful as a raw material for hepatitis A vaccine virus.

DESCRIPTION OF DRAWINGS

FIG. 1 is a diagram illustrating a method for producing hepatitis A virus (HAV) for vaccine preparation according to a method of the present invention. The HAV may be rapidly and stably amplified by obtaining a seed virus from a host cell transfected with a vector containing an HAV gene, infecting the seed virus in the same host cell and subculturing the same.

FIG. 8 illustrates a result of relatively comparing virus proliferation in host cells A and B by measuring the absorbance of the virus titer from the infected host cell lysate and culture supernatant harvested at each passage of 6 times through ELISA.

MODES FOR THE PRESENT INVENTION

Figure 2:
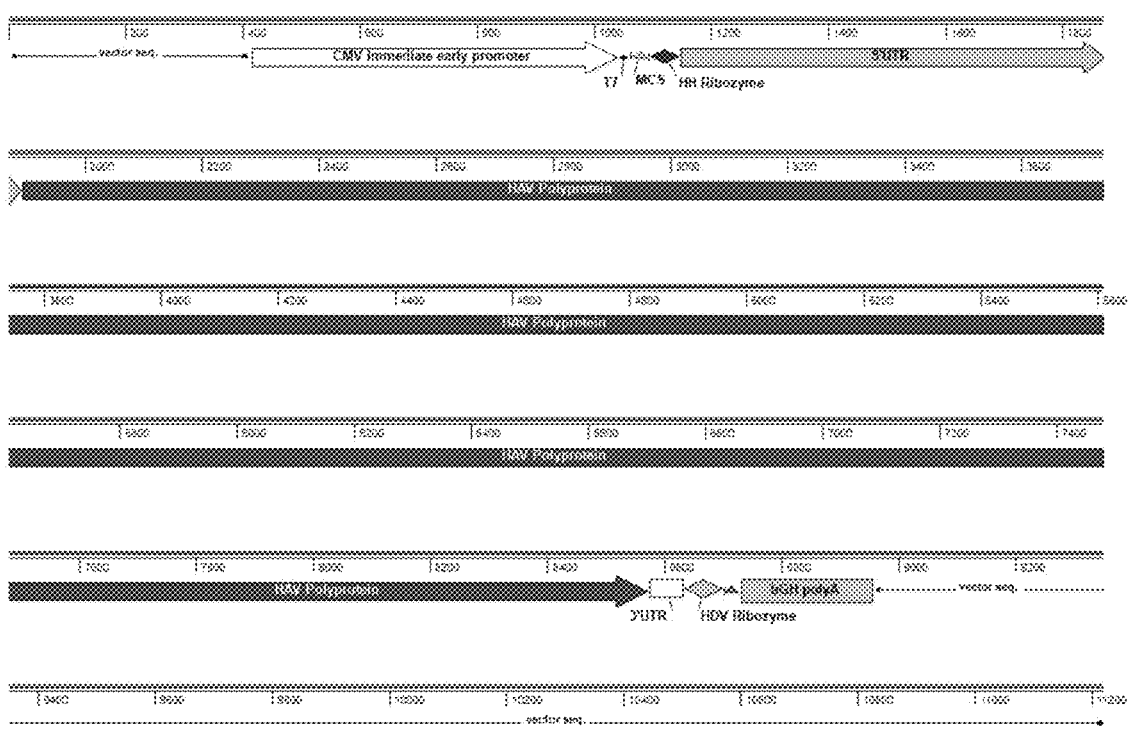
FIG. 2 is a diagram illustrating a cleavage map of the vector used for host cell transfection for preparing the seed virus in the present invention.

Hereinafter, the present invention will be described in detail by the following Examples. However, the following Examples are just illustrative of the present invention, and the contents of the present invention are not limited to the following Examples.

Experiment Method

An experimental method performed in the present invention was summarized in FIG. 1.

1. Gene Synthesis and Vector Preparation

In the present invention, a nucleotide sequence of an HAV gene used for gene synthesis was shown in SEQ ID NO: 1. The HAV gene comprised a nucleotide sequence functionally in order of a 5' untranslated region (UTR), a polyprotein gene, and a 3' UTR. A nucleotide sequence of a CMV promoter-T7 promoter (SEQ ID NO: 2), a multiple cloning site (MCS, SEQ ID NO: 3), and a hammerhead (HH) ribozyme (SEQ ID NO: 4) was included in the 5'-terminal direction of the HAV gene and a nucleotide sequence of hepatitis delta virus (HDV) ribozyme (SEQ ID NO: 5), MCS (SEQ ID NO: 6), and bGH polyA terminator (SEQ ID NO: 7) was positioned in a 3'-terminal direction. The nucleotide sequence including all other functional regions such as the HAV gene, the promoter, and the like consisting of the nucleotide sequence of SEQ ID NO: 1 was defined by SEQ ID NO: 8.

The synthesized hepatitis A virus gene of SEQ ID NO: 8 was cloned into a pUC57 vector using KpnI (GGTACC) and SalI (GTCGAC) restriction enzymes. The completed plasmid construction map was shown in FIG. 2, and was referred to as an HAV expression vector.

2. Transfection Using HAV Expression Vector

MA104 (ECACC, 85102918) and Vero (WHO) (ECACC, 88020401) cell lines were prepared in a 6-well culture plate in a EMEM (Lonza) medium containing 10% and 5% FBS under a condition of $2 \times 10^5$ cells/well/2 mL, respectively, and a Serum Free Vero cell (serum-free adaptive cell derived from Vero (WHO), SF-Vero) was prepared in a serum-free EMEM medium under a condition of $4 \times 10^5$ cells/well/2 mL, and incubated in a 5% $CO_2$ incubator at 37° C. The medium used for cell preparation became a culture medium for each cell.

After 18 to 24 hours, the culture medium was removed from the culture plate, washed twice with 2 mL of DPBS, and the culture medium was added to each well by 2 mL. 1.0 μg of an HAV expression vector (plasmid), 35 μL of Lipofectamine LTX-Plus (ThermoFisher), and 960 μL of Opti-MEM (ThermoFisher) were mixed in a conical tube and left at room temperature for 15 minutes. The mixture was added to each plate well by 200 μL and incubated in a 5% $CO_2$, 37° C. incubator. After 24 hours, the supernatant of all cells was removed, and the culture medium of the MA104 and Vero cell lines was exchanged with EMEM containing 2% FBS (2% FBS-EMEM), and the culture medium of the SF-Vero cell line was exchanged with 2 mL of a serum-free EMEM medium (SF-EMEM), and the cell lines were incubated for 3 weeks in a 35° C., 5% $CO_2$ incubator. The incubated MA104, Vero and SF-Vero cells were harvested in 500 μL of the EMEM medium, suspended, and frozen/thawed three times. In order to remove the remaining crushed cell debris, after centrifugation at 10,000 g for 1 minute, only the supernatant was harvested again and set as virus P0 (seed virus).

3. Blind Passage for Virus Rescue

When infection passage as first blind passage P1 was performed using P0 virus, $1×10^6$ cells/5 mL of MA104 and Vero, and $5×10^6$ cells/5 mL of SF-Vero were prepared in a T25 flask before 24 hours of infection. At the time of P1 to P4 infection passages, in the T25 flask, the MA104 and Vero cells at a concentration of $7×10^5$ cells/5 mL and SF-Vero cells at $1×10^6$ cells/5 mL were incubated in a culture medium at 37° C. and 5% $CO_2$. After 24 hours, the culture medium was removed from the prepared cells, and 5 mL of DPBS was added and washed twice immediately before infection. In P5 and P6 infection passages, before one day of infection passage from P4, $5×10^6$ cells/30 mL of MA104 and Vero cells and $8×10^6$ cells/30 mL of SF-Vero cells were prepared in the T175 flask, and the medium was removed from the cells prepared just before infection in the same manner and washed twice with 30 mL DPBS.

An EMEM medium containing 2% FBS was a virus infection medium for the MA104 and Vero cell lines, and EMEM without FBS was used as an infection medium for the SF-Vero cell line. 5 mL of each cell infection medium was used for P1 to P4 infection passages, and 35 mL of the infection medium was used for P5 and P6 infection passages. In P6 passage, the infection passage was performed using five T175 flasks. The prepared P0 sample was added to the prepared cells and left at 35° C. and 5% $CO_2$ for 1 hour, and then 5 mL (35 mL) of the infection medium was added.

The culture medium was exchanged every 7 days for 21 days after infection with the P0 sample, and the infected cells were maintained. On day 21 after infection, a cell lysate was harvested and freezing/thawing (−70° C./37° C.) was performed 3 times as in P0 harvest, and then cell debris was removed and centrifuged, and only a supernatant was harvested and used as a virus culture medium, and set as passage 1 (P1). During the passage from P0 to P1, the medium was exchanged weekly, but during the passage from P1 to P6, the medium was exchanged only on day 7 after infection. A total of 6 passages were successively performed by setting 20 to 21 days as one passage period. The processes of the cell infection and passage described above were illustrated in FIGS. 3A and 3B.

After one passage was completed, the culture supernatant and the cell lysate were harvested from the virus-infected flask, respectively. When the cell lysate was harvested, 2 mL of a Trypsin-Versene (Lonza) solution was added to the flask from which the supernatant has been removed, washed and removed, and then 2 mL of a Trypsin-Versene solution was added again, left in a 37° C. incubator for 5 minutes, and the cells were separated. 2 mL of a Trypsin-Versene suspension in which the cells were suspended was transferred to a conical tube, and centrifuged to harvest a cell pellet.

The cell lysate (pellet) was added in EMEM 1 mL (T25, P1-P4) or 5 mL (T175, P5) and centrifuged after freezing/thawing three times, and then prepared as a supernatant (cell lysate sample) from which the cell debris was removed. After centrifugation with the harvested culture supernatant of each infection passage, 200 μL of the cell lysate sample was transferred to a microcentrifuge tube for virus titer analysis and frozen until analysis. All of the remaining cell lysate sample except for analysis was used for the next infection.

The titers of P1 to P5 were measured by ELISA qualitative analysis, and at passage 6 (P6), the culture supernatant was removed, all the infected cells were harvested, suspended in 5 mL of serum-free EMEM, and centrifuged after freezing-thawing 5 times to remove the cell debris, and then only the supernatant was harvested and stored as a seed virus. A titer of P6 virus was measured by ELISA qualitative analysis.

4. Confirmation of Cytopathic Effect of Blind Passage Process

The cytopathic effect (CPE) of the host cell according to viral infection was performed by a microscope examination. In the MA104 and Vero cell lines, the cytopathic effect by the virus was not shown until the P4 passage, but CPE caused by the virus such as cell lysis and detachment was confirmed from P5 passage, and the SF-Vero cell line showed mild CPE after P3 passage.

5. HAV Antigen Analysis ELISA

The HAV antigen in the sample harvested during virus blind passage was measured through qualitative and quantitative analysis. For the qualitative analysis, HAV-specific ELISA was performed to confirm the antigen by absorbance (optical density, 450 nm), and for the quantitative analysis, a standard curve was prepared by applying a standard product (Inactivated HAV BRP, 1350 IU/mL, Y0001192, EDQM), and the HAV virus titer (antigen content) in the sample was measured. An assay kit HAV-Antigen ELISA Kit (Mediagnost, E12) was used, and a virus titer unit was expressed as IU/mL according to the standard product. The commercial hepatitis A virus strain (ATCC VR-1402) used was also quantified by the same method.

6. Transmission Electron Microscopy (TEM)

Figure 3A:
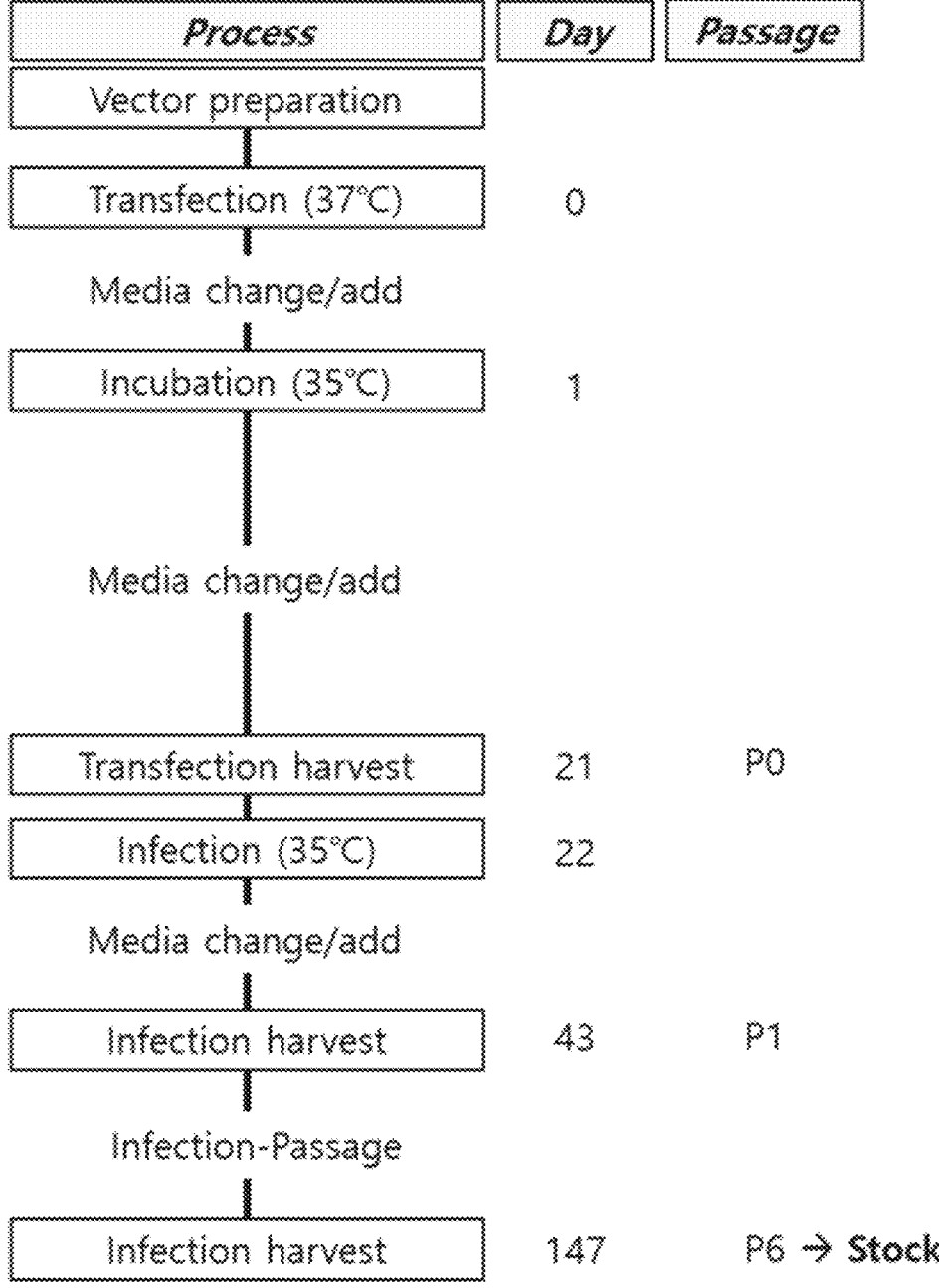
FIGS. 3A and 3B are diagrams illustrating a method for preparing HAV from a MA104 cell and a Vero cell (FIG. 3A) and a method for preparing HAV from a serum-free adaptive Vero cell (SF-Vero) (FIG. 3B) step by step according to the method of the present invention.
Figure 3B:
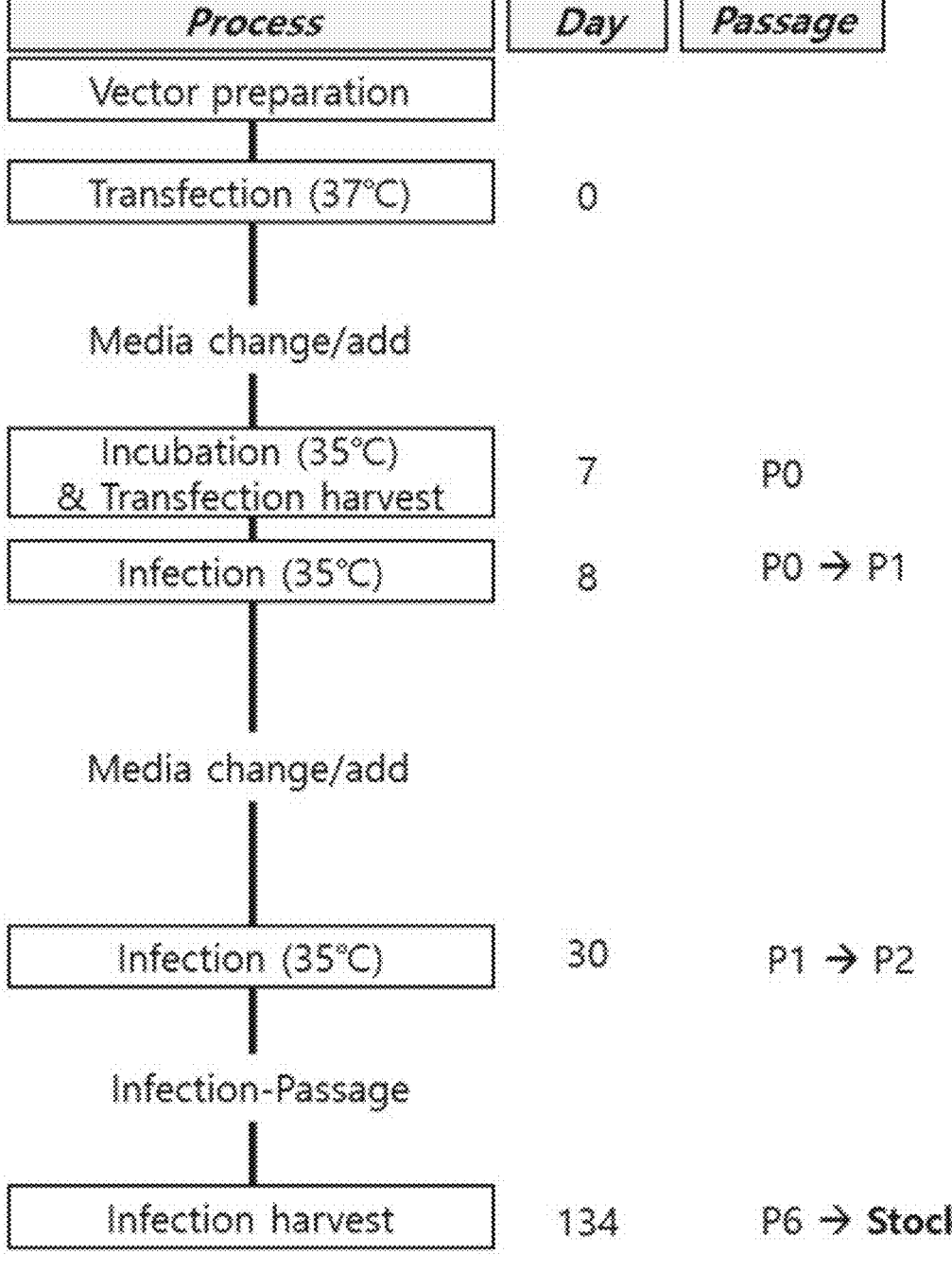
Figure 4:
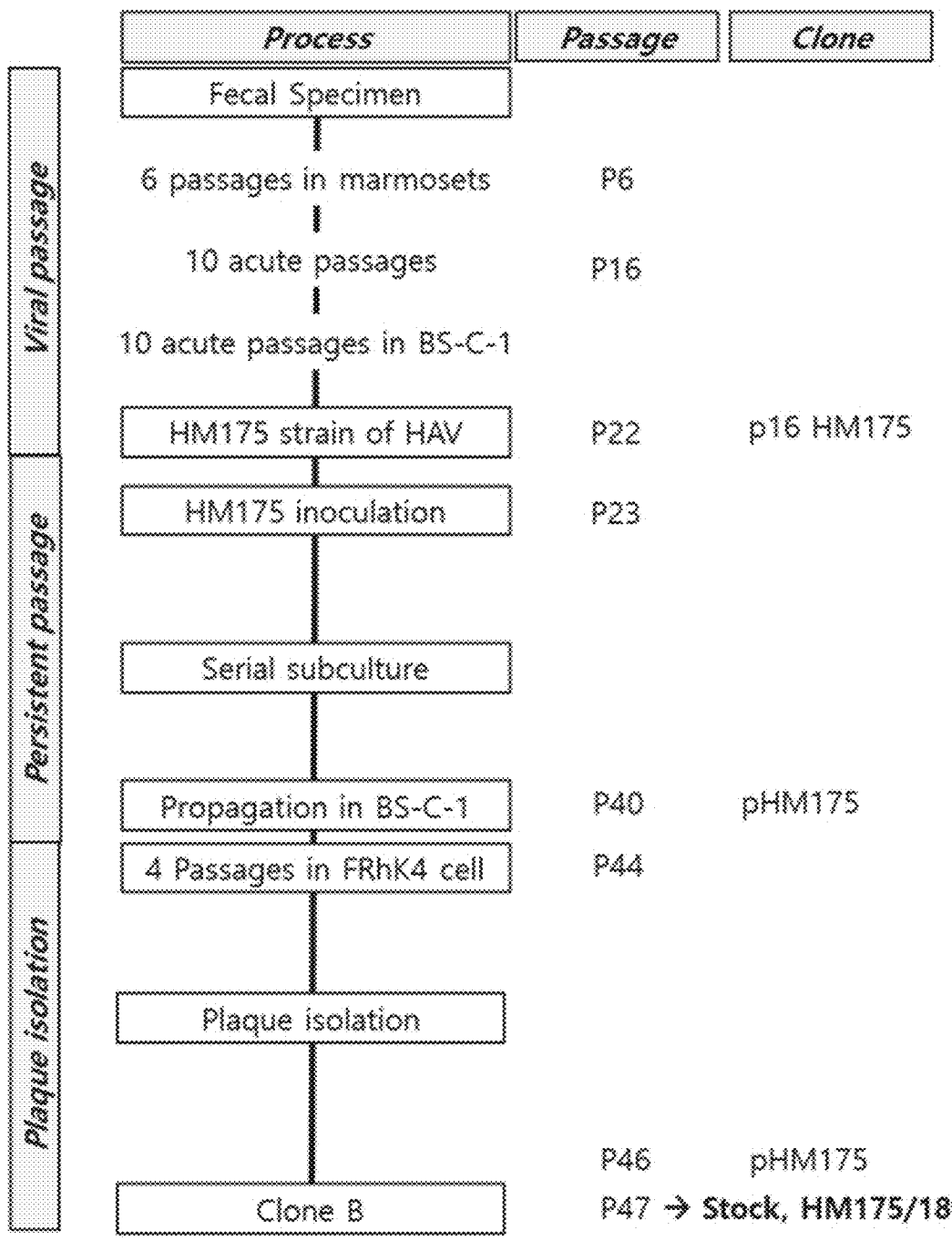
FIG. 4 is a diagram illustrating a method for preparing HAV step by step in the related art.

A transmission electron microscope image was observed using a part of the cell lysate harvested after subculturing of P6 in FIGS. 3A and 3B. Negative staining was performed with 2% uranyl acetate for 15 seconds by using a formvar-carbon coated EM grid and observed with a transmission electron microscope (JEM-1011, JEOL), and virus particles were identified with Camera-Megaview III Imaging equipment.

7. Immunofluorescence Assay (IFA)

MA104 and Vero cells under the condition of $5×10^3$ cells/well/0.5 mL and SF-Vero cells at a concentration of $8×10^3$ cells/well/0.5 mL were suspended and prepared in each culture medium in a 24-well culture plate, and incubated for 24 hours at 37° C. and 5% $CO_2$ conditions. The medium was removed from the incubated cells and washed by adding DPBS at 300 μL/well. The seed virus prepared in FIG. 3 was diluted with the infection medium of each cell, treated in the cells at a concentration of 0.1 IU/well, and 0.5 mL of the infection medium was added to each well and incubated in a 35° C. and 5% $CO_2$ incubator. On day 7 from the day of infection, the supernatant of the cells was fully removed and washed twice with 0.5 mL DPB. All the DPBS remaining in the cells was removed, 0.2 mL of a 3.7% formaldehyde solution was added, and then left at room temperature for 30 minutes. The formaldehyde solution was removed and washed three times with DPBS in the same manner as described above. A 0.2% Triton X-100 buffer solution was added at 250 μL/well, left at room temperature for 5 minutes, and then washed 3 times with 0.5 mL DPBS. A primary antibody (Anti-HAV Surface Ag, Raybiotech) was diluted to ½00 in PBS, added by 250 μL/well, and reacted at room temperature for 1 hour. Thereafter, a secondary antibody (Goat anti-Mouse IgG Alexa488, ThermoFisher) was diluted to ¼000 and added to the cells in the same dose as the primary antibody treatment dose, left at room temperature for 1 hour, then washed with DPBS 5 times and removed. DPBS was added to the cells at 250 μL/well, and the cells were photographed with a fluorescence microscope (Magnification 100×, Eclipse Ts2-FL, Nikon).

8. Confirmation of Seed Virus Infection (Infection Test)

The infection patterns of the seed virus prepared in FIGS. 3A and 3B and a commercial hepatitis A virus strain (ATCC VR-1402) were compared with each other. To this end, the virus titer (content) of the commercial virus strain was quantified by ELISA described in this patent. Before 24 hours of virus infection, the MA104 and Vero cell lines were prepared at $2 \times 10^6$ cells in a T75 flask, and the SF-Vero cell line was prepared at $3.5 \times 10^6$ cells in a 12 mL culture medium. The seed virus and the commercial virus strain were suspended in al mL infection medium by 2.0 IU, washed with 10 mL of DPBS and added to each cell in the T75 flask prepared. After 1 hour reaction in a 35° C., 5% $CO_2$ incubator, 11 mL of the infection medium was added and incubated. The cells were incubated for 21 days, and on 7 day after infection, the medium was exchanged with a fresh infection medium. One viral infection passage of the 21-day incubation was performed a total of 10 times, the sample harvest and serial infection passages for virus content analysis were the same as those in blind passage, and when the cell lysate sample was harvested, the cells were finally suspended in 5 mL of serum-free EMEM and used as a sample for the next infection passage.

In addition, the MRC-5 (ECACC, 05011802) cell line was prepared in a T75 flask with a total number of $8 \times 10^6$ cells/12 mL, and SF-Vero was prepared at a cell concentration of $3.5 \times 10^6$ cells/12 mL, and the seed virus prepared in FIG. 3B was subjected to a total of 6 consecutive infection passages under the same conditions as in the T75 flask infection above. Virus titers (contents) in some of the supernatants and some of the cell lysate samples harvested at each viral infection passage were measured and compared. The culture medium of the MRC-S cell line was used to contain 10% FBS in the EMEM medium and 2% concentration of the infection medium. The method of harvesting the supernatant and cells after virus infection was the same as the method of repeating freezing/thawing, and the detailed method was the same as described in the method of performing blind passage.

9. Growth Confirmation Test of Seed Virus

Before one day of infection, SF-Vero cells were seeded in a T175 flask at $2 \times 10^7$ cells/35 mL and incubated at 37° C.

and 5% $CO_2$ conditions. All 9 T175 flasks of the same cell density were prepared, 8 flasks were infected with virus, and the rest was set as a normal cell control. After the culture medium was removed from all the flasks on the day of infection, in each flask, the cells were washed with 30 mL of DPBS. A virus infection solution containing 15 IU of SF-Vero-derived seed virus in 35 mL of the culture medium was prepared and added to the washed T175 flask. 15 IU of SF-Vero-derived seed virus was infected equally in a total of 8 flasks. While the infected cells were incubated in a 35° C. and 5% $CO_2$ incubator, the supernatants and the cell lysates were harvested on 3, 7, 10, 14, 17, 21, 24, and 28 days post-infection (dpi), respectively, to measure the virus titers (contents)

10. Incubation of Seed Virus Cell Factory

The additional infection passage of the seed virus derived from each cell was performed in the T175 flask in the same manner and then performed to passage 11 (MA104, Vero) and passage 12 (SF-Vero) to increase the cell adaptability of the virus and infected cells in the corresponding process were harvested. In the method of additional infection passage, the first seed virus harvested from P6 was infected and incubated twice in the T175 flask to obtain a virus of passage P8, and when infected with P9, the virus sample obtained from P8 was quantified to be infected at a concentration of 15 IU/T175. Similarly, the virus was passaged by repeating infection-harvesting until P11 and P12. The P11 (MA104, Vero) and P12 (SF-Vero)-passage viruses of the seed virus were quantified and the virus corresponding to 500 IU was dispensed into a separate cryovial. The commercial virus was infection-passaged to P11 (MA104, Vero) and P12 (SF-Vero) in the same manner as the additional infection passage using the commercial virus sample obtained after 6 passages of FIG. 6 to obtain a virus. In the additional infection passage, the supernatant was not harvested, and only the infected cells were harvested, cell-crushed with a Sonifier for 40 seconds, centrifuged, and then only the supernatant was harvested and used. The seed virus and the commercial virus were used for host cell infection of CF10 (6320 $cm^2$, ThermoFisher) in equal amounts of 500 IU, respectively. The infection method in CF10 was as follows. MA104, Vero, SF-Vero cells were prepared in a culture medium of $2.0 \times 10^8$ cells/1.5 L. After 16 to 18 hours, the culture medium was removed, and the cells were washed once with 500 mL of DPBS and removed. A virus infection solution was prepared by adding 500 IU of the virus prepared in 200 mL of the EMEM medium, and was added to the washed CF10. The virus infection solution was incubated for 60 minutes at 35° C. and 5% $CO_2$ conditions, and the flask was tilted every 15 minutes to allow the virus diluent to be evenly adsorbed to the cells. After virus adsorption, 1.5 L of the infection medium (MA104, Vero: 2% FBS-EMEM, SF-Vero: SF-EMEM) of each cell was added, and incubated for 21 days at 35° C. and 5% $CO_2$ conditions. On day 7 of virus incubation, the medium was exchanged with a fresh infection medium.

After infection, the harvest process of virus-infected incubation in CF10 was as follows. After infection, the supernatant was removed from the CF10 container. CF10 was washed with 500 mL of DPBS and removed, and 200 mL of TrypLE Express (ThermoFisher) was added and reacted in a 37° C. incubator for 3 to 5 minutes. 200 mL of serum-free EMEM was added, and about 400 mL of the infected cell suspension was harvested in a 2 L square bottle. The harvested suspension was centrifuged at 5000 g for 10 minutes, the supernatant was removed, and only the cell pellet was recovered. 100 mL of a phosphate buffer (50 mM, pH 7.0) was added to the cell pellet, suspended, and then sonicated with a Sonifier (SFX550, Branson) (amplitude 40%, 2 minutes) to be cell-lyzed. About 100 mL of the cell lysate was centrifuged (5000 g, Allegra X-15R, SX4750A), and the supernatant was transferred to a new sterile 1 L Square Bottle. After centrifugation, some 100 µL of 100 mL of the supernatant was stored and used for ELISA analysis. 400 mL of a phosphate buffer (50 mM, pH 7.0) was added and used in a purification process. The cell lysate derived from MA104 and Vero was stored separately, and the lysate of virus-infected cells incubated in SF-Vero was used for antigen purification for animal test administration.

11. Virus Purification and Inactivation

The recovered cell lysate was sequentially purified using a capsule filter (Sartopure PP3, 5 µm, Sartorius Stedim) and a depth filter (Supra 50, 050PDH4, PALL). The purified harvest was buffer-exchanged with a phosphate buffer (50 mM, pH 7.0) using a 100 kDa ultrafiltration/diafiltration (UF/DF) filter (Pellicon® 2 Mini, P2B100A01, Merck Millipore), filtrated and 10-fold concentrated, and then treated with benzonase (1 unit). Ion exchange chromatography (IEC) was performed with a DEAE Sepharose® Fast Flow (GE Healthcare) column equilibrated with the phosphate buffer (50 mM, pH 7.0) at a rate of 10 mL/min. About 200 mL of fractions were collected, buffer-exchanged with a phosphate buffer (50 mM, pH 7.0) using a 10 kDa UF/DF filter (Pellicon® 2 Mini, P2B010A01, Merck Millipore), and concentrated 5-fold. The concentrate was subjected to size exclusion chromatography (SEC) at a rate of 1 mL/min using a HiPrep 26/60 Sephacryl S-200 HR (GE Healthcare).

After SEC was performed, about 40 mL of antigen fraction was collected and concentrated 80-fold using a 10 kDa filter (Pellicon® 2 Mini, P2B010A01, Merck Millipore) to obtain a purified HAV antigen. Formaldehyde was added to the antigen obtained for virus inactivation at a concentration of 270 to 370 µg/mL and reacted at 37° C. for 5 days. Thereafter, the antigen was diafiltrated with a 10 kDa filter and sterilization-filtrated with a 0.22 µm filter (Millipak® Gold). Before 24 hours of each administration in the animal test, alum hydroxide was suspended in an adsorption buffer (pH 7.1 to 8.0), mixed with the antigen, and stirred at 4° C. for 16 hours or more.

12. Animal Experiment

The Alum adsorbed antigen was administered to mice (BALB/c, 4-week-old, 10 subjects per group). As a control of the animal experiment, a commercial HAV vaccine (HAVRIX®, GSK) was used, and an antigen (3.0 IU and 1.5 IU) administered to the mice and the dose of the control (144 EL.U and 72 EL.U, ELISA Unit) were set to ⅒ of a dose of persons (adult and infant) presented in the commercial vaccine. The dose setting of the administered antigen was adjusted to the same level by measuring and comparing the antigen and the amount thereof of the present invention after isolating only the antigen by dissociating the alum salt bound to the control (commercial vaccine). In the animal experiment, the antigen was administered 3 times at an interval of 2 weeks by intramuscular injection (IM). After administration, serum was isolated from the mouse whole blood to measure an anti-total HAV antibody titer. 97/646 (NIBSC, International Standard for Anti-Hepatitis A, Immunoglobulin) was set as a standard control material, and during measurement, anti-HAV ELISA (E10, Mediagnost), or anti-Hepatitis A Virus IgG ELISA (4660, ALPHA Diagnostic International) was used.

Experimental Results

In the present invention, a gene expression cassette was designed to express a HAV gene, and the corresponding cassette was synthesized to obtain a cassette expression vector. A synthetic-based HAV expression vector was transfected into three types of cell lines MA104, Vero, and SF-Vero, a gene-transfected cell (transfectant) was lyzed to be infected to the same cell, and blind passage or virus infection passage was performed until the virus particles were confirmed to isolate the virus. From this, a predetermined amount of virus was confirmed to be prepared as a seed virus that can be used for future vaccine production and research. The seed virus was prepared by subculturing only 6 times, and it was confirmed that the seed virus was prepared in a sterile state by performing *mycoplasma* and sterility test after preparation.

In the case of existing commercial vaccines, in order to prepare a virus (master seed lot) to be used for vaccine production, a cell culture adaptation process of the virus was performed several times to establish the virus by subculturing in MRC-5, which required primary AGMK culture and serum. Among seed viruses prepared by the method, a seed virus (926 IU/mL) prepared from a serum-free vaccine-producing cell line (SF-Vero) was a virus derived from a cell line for vaccines, and had high applicability for commercial vaccine development. After the corresponding seed virus was amplified, purified, and inactivated to remove infectivity, adsorbed to an adjuvant and then administered to mice, it was confirmed that the antiserum titer for the administered antigen of the patent was similar to that of the commercial vaccine.

Figure 5A:
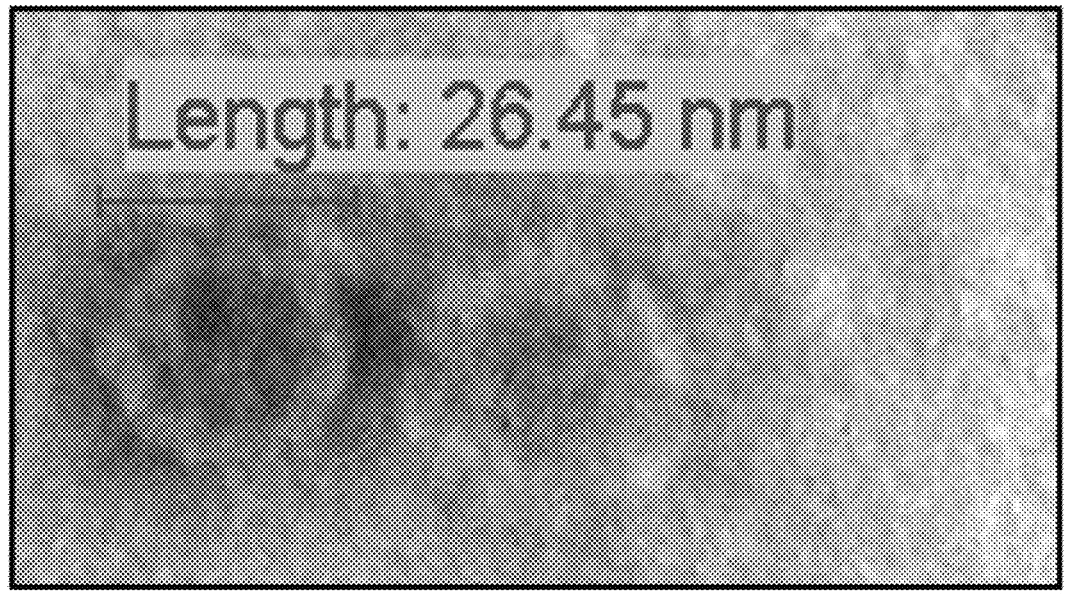
FIGS. 5A to 5C are diagrams observing viruses isolated at passage 3 (P3) after infecting MA104 (FIG. 5A), Vero (FIG. 5B), and SF-Vero (FIG. 5C) with the seed virus prepared according to the method of the present invention through a transmission electron microscope (TEM).
Figure 5B:
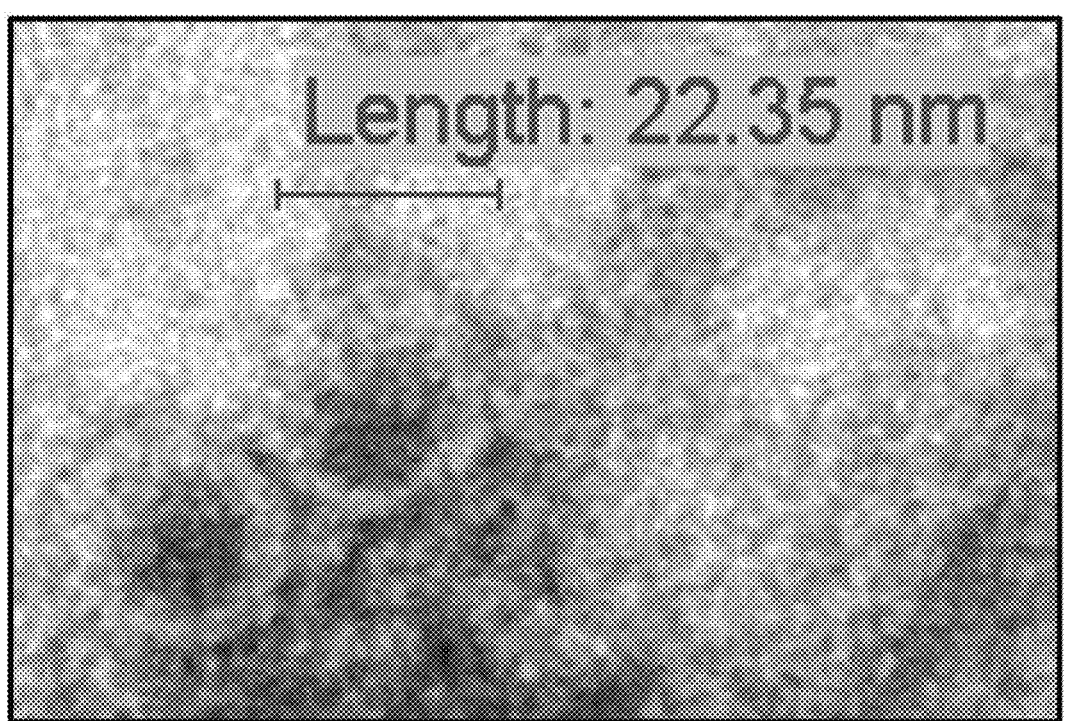
Figure 5C:
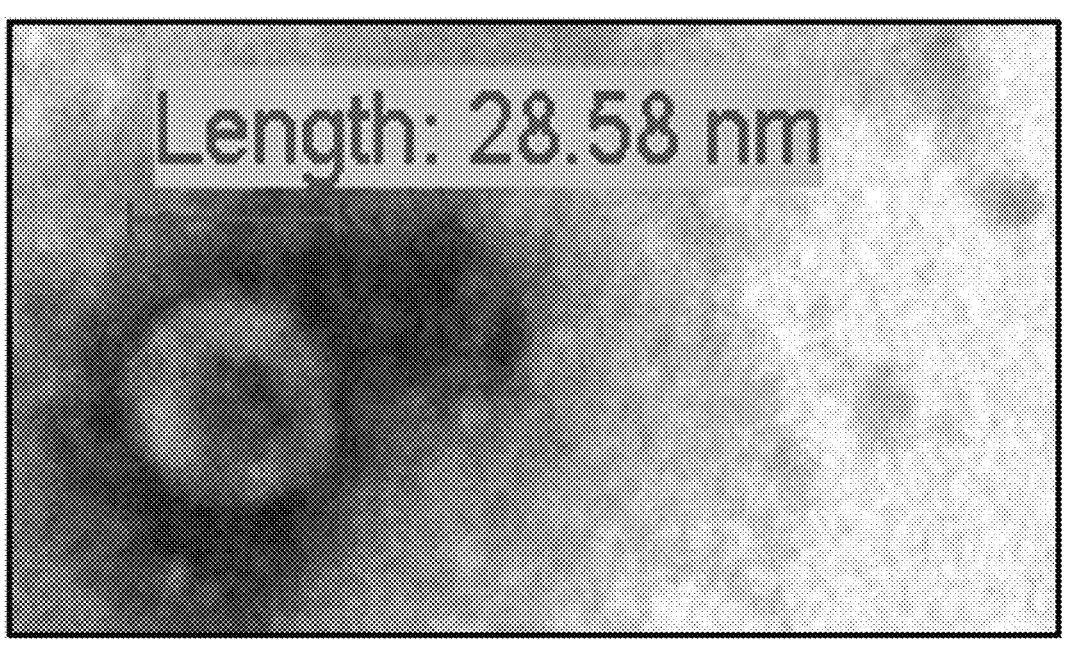
Figure 6:
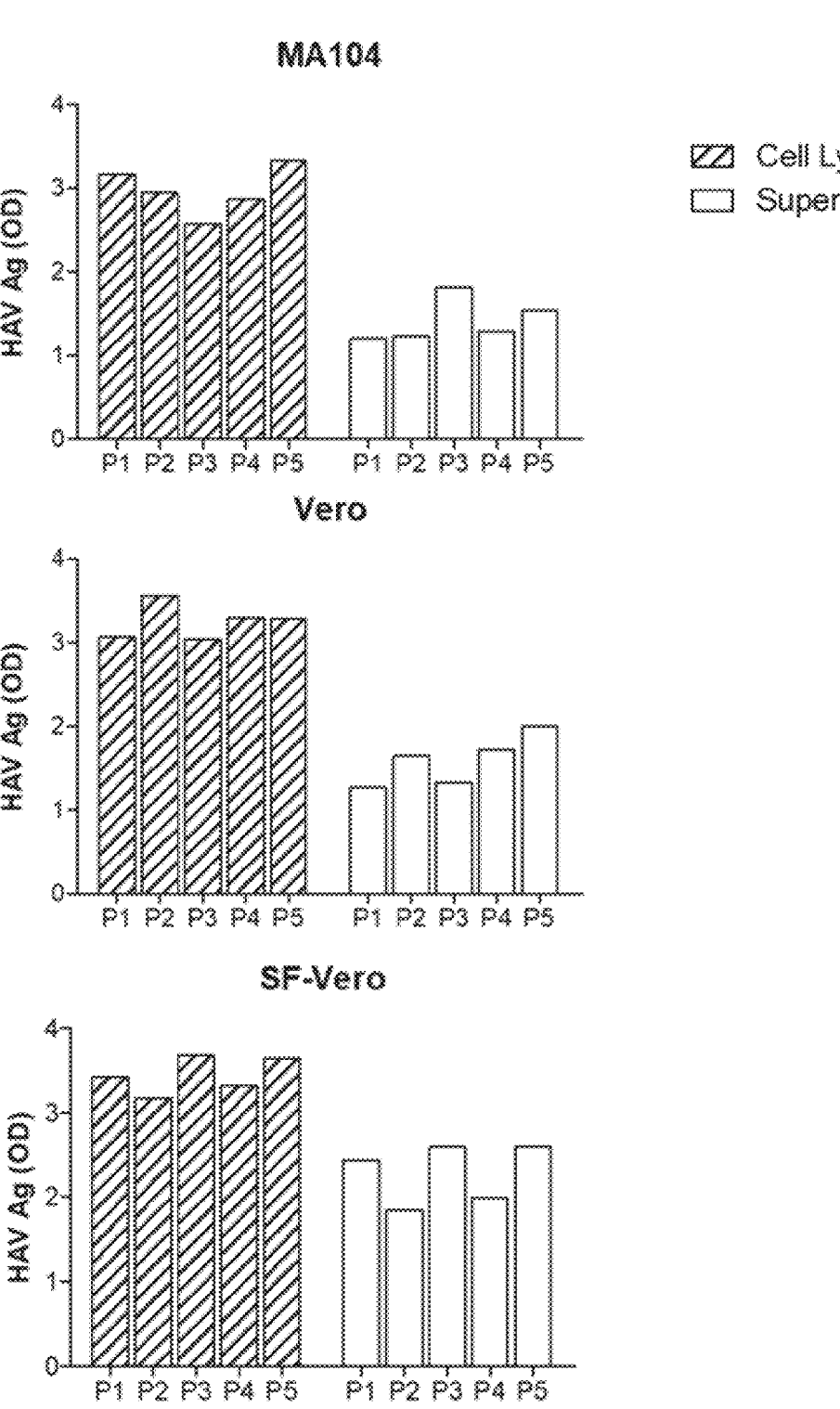
FIG. 6 is a result of confirming a virus content (titer) identified in passage 5 (P5) in passage 1 (P1), which is a blind passage step for virus rescue after P0 during the process of FIGS. 3A and 3B of the present invention. Virus titers in cell lysates and culture supernatants at each passage of P1 to P5 were measured as absorbance values.
Figures 7A, 7B:
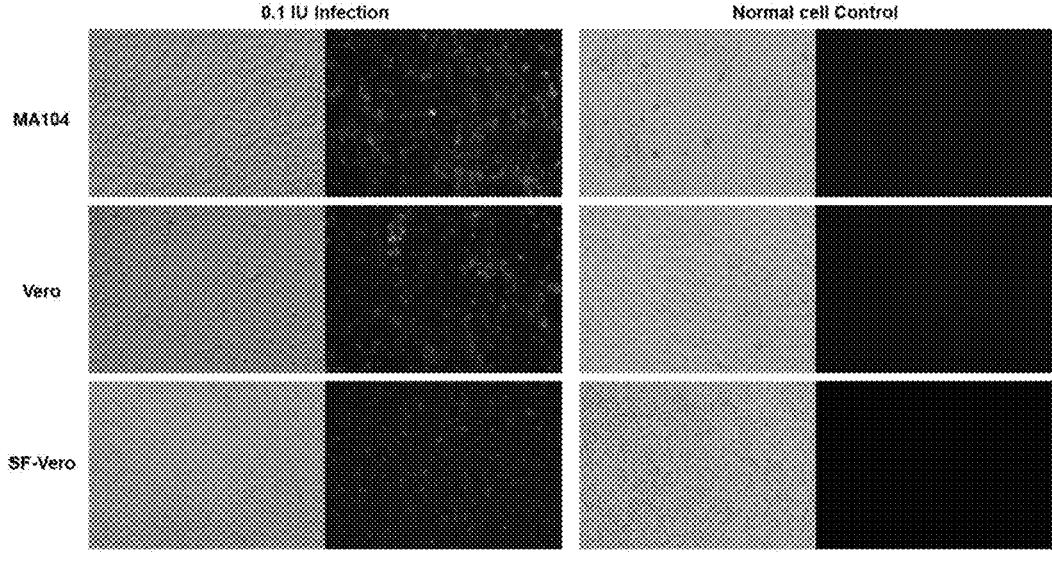
FIGS. 7A and 7B illustrate a result of quantitative analysis of the virus content (titer) identified from a cell lysate sample isolated from p6 in the process of FIGS. 3A and 3B of the present invention (FIG. 7A), and a result of detecting viruses infected in the cells with immunofluorescence assay (IFA) after infecting MA104, Vero, and SF-Vero cells with the seed virus prepared in P6 subculturing (FIG. 7B).

The method for producing the virus using the above-described vector and the HAV expression cassette used for virus production were schematically illustrated and described in FIGS. 1 and 2, respectively. In the process of FIG. 1, two incubation processes performed in the MA104 and Vero cell lines and in the SF-Vero cell line were listed, and the processes of transfection and blind passage were illustrated in FIGS. 3A and 3B together with a required period. After the infection passages from P1 to P5, the virus titers (contents) in the supernatant and the cell lysate harvested and measured at each passage were confirmed as illustrated in FIG. 6. Even after several passages after transfection, the virus was confirmed by ELISA detection, and it was confirmed that the virus was stably amplified in the supernatant and cell lysate samples. The relative detection amount of virus was confirmed to be higher in the cell lysate than in the supernatant, which may reflect the non-lytic HAV characteristics. Immediately after the P6 subculturing, which was the next time, the virus particles were confirmed from the cell lysate by electron microscopy (FIGS. 5A to 5C), the virus content was quantified and confirmed as 2371 IU/mL (MA104), 586 IU/mL (Vero), and 926 IU/mL (SF-Vero) (FIG. 7A). Referring to the fact that the MA104 cell line was used for infection studies of enteric viruses proliferated in the gastrointestinal tract, such as hepatitis A virus (JH Lee et al., 2013), the seed virus for research was amplified from the cell line and used for securing. Vero and SF-Vero cell lines had the same origin, but their virus culture conditions were varied as the condition of the presence or absence of serum. In particular, SF-Vero cells were selected together to confirm that the virus of the present invention may be smoothly amplified even in serum-free conditions. As the content of the seed virus, it was confirmed that the SF-Vero-derived seed virus incubated and isolated in the serum-free culture condition had a relatively high content compared to the Vero cell-derived seed virus. The prepared seed virus was infected with the content of 0.1 IU/well in a 24-well plate, and the infectivity of the virus was confirmed by immunofluorescence on day 7 (FIG. 7B).

Figure 8:
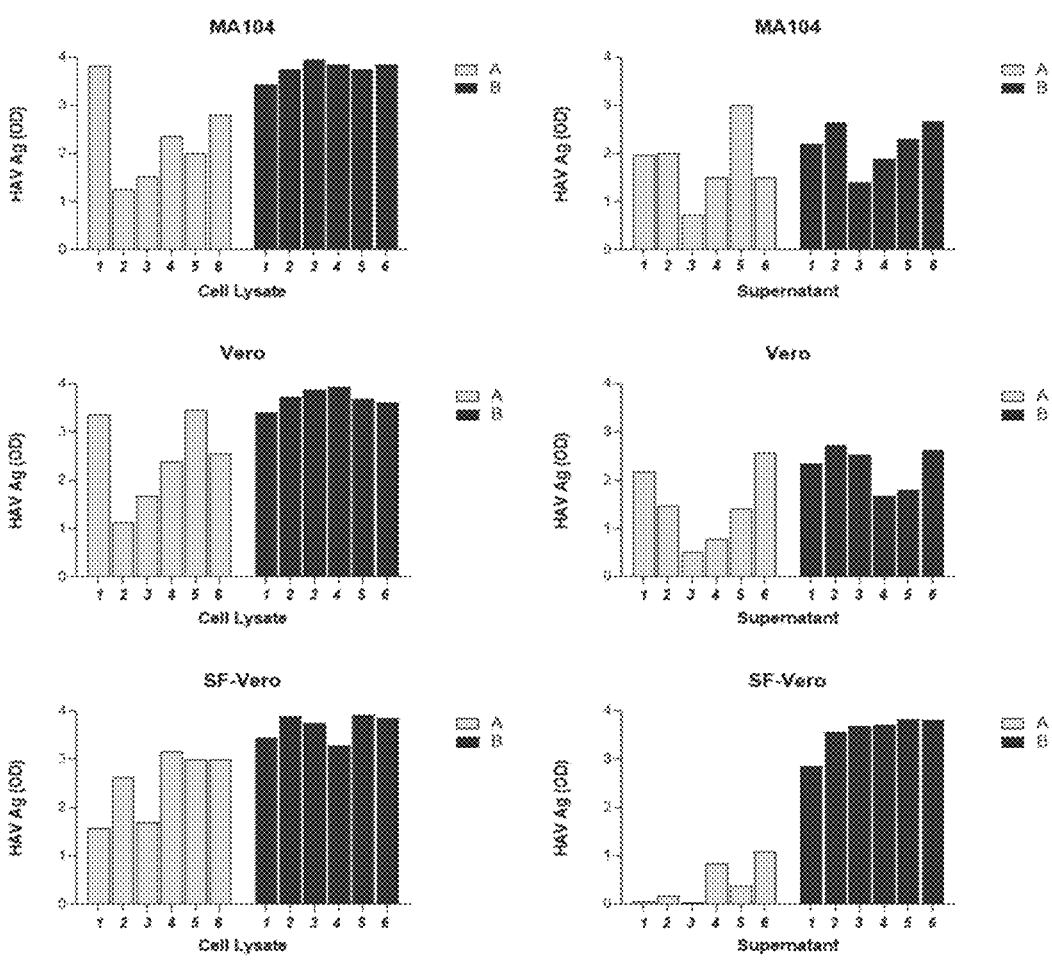
FIG. 8 is a diagram of measuring virus contents after continuously performing virus infection passages 1 to 6 after infecting host cells MA104, Vero, and SF-Vero with commercially available HAV (FIG. 8A ⬜ ) or infecting the same host cells with the seed virus prepared according to the method of FIGS. 3A and 3B (FIG. 8B ▨ ). In addition.

Three types of the prepared seed virus of FIG. 7A and a commercial virus (ATCC stock, 227 IU/mL) were infected with 2.0 IU as described in the method for confirming the seed virus infection in experiment method 8, and compared with the degree to be amplified when the seed virus of the present invention and the commercial virus were infected to the same cell line. Viruses were detected from the supernatant and the cell lysate of the infected culture that performed a total of 6 consecutive infection passages, and as compared to the commercial virus strain (FIG. 8A), it was confirmed that the seed virus (FIG. 8B) of the present invention had a stable and relatively high virus titer (FIG. 8).

Figure 9A:
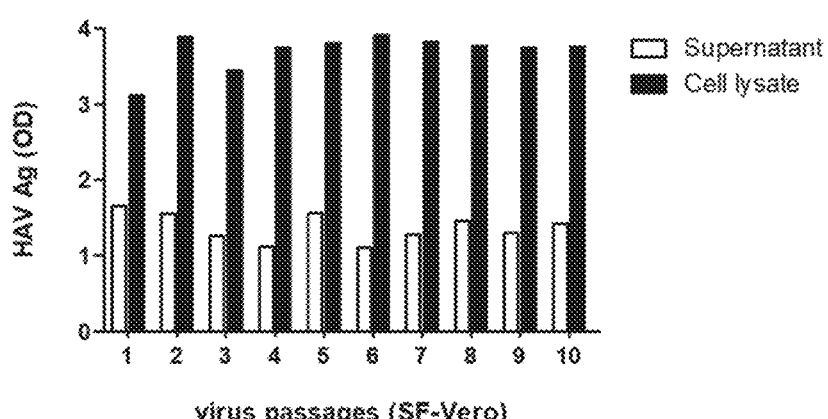
FIGS. 9A and 9B are results of confirming the virus titer in the supernatant and the cell 10 times after infecting an SF-Vero cell line and an MRC-5 cell line with the seed virus prepared according to the method of FIG. 3B.
Figure 9B:
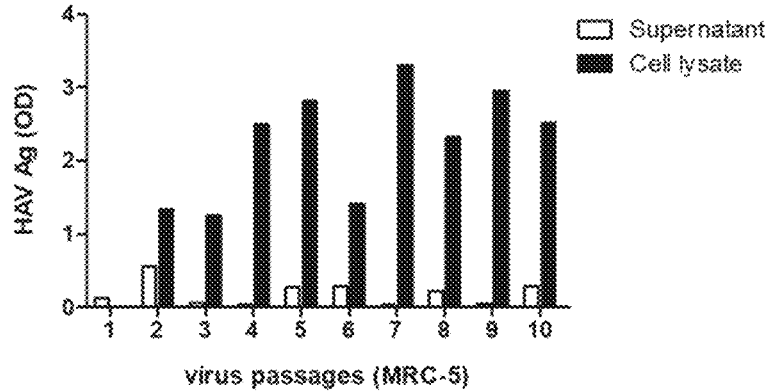

In addition, the MRC-5 cell line that has been used as a production cell for the existing hepatitis A vaccine and required serum during incubation and the SF-Vero cell line, a vaccine-producing cell in serum-free culture used for virus production and infection in the present invention were set as infection cells and compared by infecting 2.0 IU of the seed virus prepared in SF-Vero of FIG. 3B. During a total of 10 passages, the supernatant and the cell lysate were analyzed by ELISA and the virus titer (content) was relatively compared with the absorbance value. As a result, the virus production in SF-Vero cells had a pattern in which the virus started to be detected from the first passage after infection, and from the second passage, the virus titer measured in the cell lysate was consistently detected in the ELISA reaction (FIG. 9A). In the passage in MRC-5, there was a passage in which virus detection in the harvested cell lysate sample was measured at a similar level, but a constant increased pattern of the virus titer was not shown. In particular, virus detection in the supernatant was low in contrast to the result of the infection passage in SF-Vero for vaccine production (FIG. 9B). Through this, it was confirmed that the seed virus prepared by the method of the present invention was amplified smoothly in SF-Vero cells, and the cell adaptability of the virus according to the culture after infection passage was higher in the SF-Vero cell line than the MRC-5 cells. The measured absorbance result values were reported together with a graph (FIGS. 9A and 9B).

Figure 10:
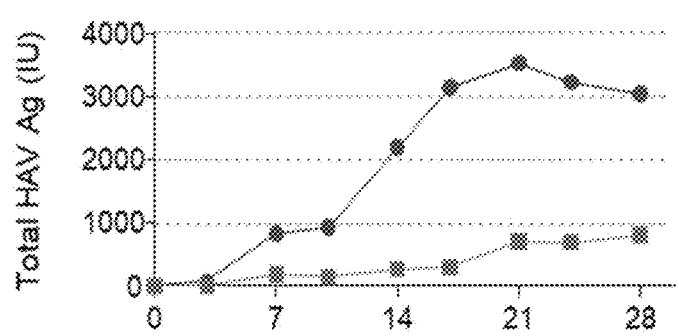
FIG. 10 illustrates confirmation of the virus titer (antigen content) according to the number of days of virus incubation in a T flask (175 cm²). In order to confirm a virus growth pattern after infection with the seed virus of the present invention, infection samples were harvested every 3 to 4 days, and virus titers were measured and illustrated from the supernatant and the cell lysate.

Before performing CF10 culture to obtain a virus to be used in an animal experiment, the SF-Vero-derived seed virus prepared in the present invention was infected in the T175 flask, and changes in virus titer (content) according to the number of days were confirmed at intervals of 3 to 4 days (FIG. 10). This was performed preferentially in order to confirm the culture period of the virus of the present invention while setting the virus content per culture unit area of the cells to be infected. As a result of measurement after virus infection, the amount of virus in the cells was increased from 10 days after infection, and like the drawings (FIGS. 6, 7A and 7B, 8, and 9), it was confirmed that the virus amplified in the cells had a high titer compared to the supernatant. In particular, the maximum virus content was confirmed around 20 to 21 days after infection. The virus amplification (3537 IU, 21 dpi) about 230 times larger than the initial infection amount (15 IU) was confirmed (FIG. 10).

Figure 11:
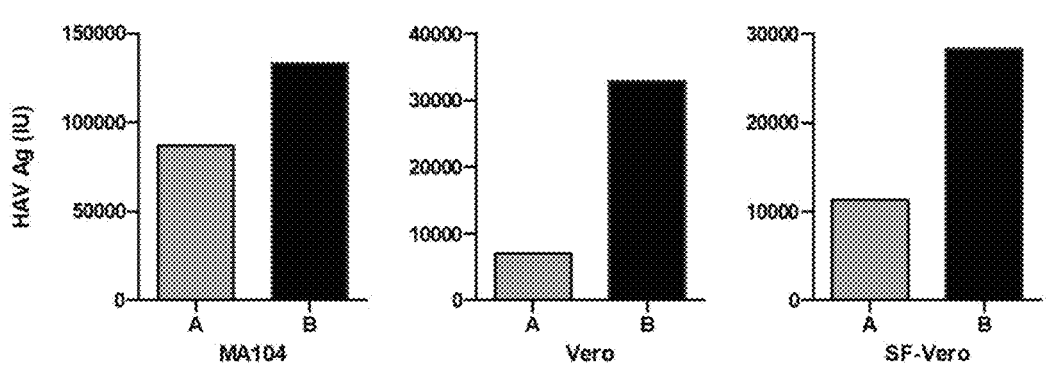
FIG. 11 illustrates a result of confirming virus titers in cell lysates of passage P11 by infecting a host cell in a cell factory 10 (CF10) culture container with commercially purchasable HAV (FIG. 11A) or infecting a host cell MA104, Vero or SF-Vero with the seed virus prepared according to the method of the present invention (FIG. 11B).

Referring to FIG. 11, as the result of measuring the virus titer obtained by incubating the seed virus and the commercial virus having the same number of infection passages of the same condition in CF10, a virus titer B prepared according to the method of the present invention and passaged was measured significantly higher than a virus titer A obtained by incubating the commercial virus obtained according a general method A requiring a long period in the same manner. The significant level means that the titer B according to the method of the prevention invention was increased in the contents of 150% (MA104, 1.53 times), 470% (Vero, 4.70) compared to (A). times) and 251% (SF-Vero, 2.51 times) as compared with the titer A on the premise of the same virus culture area and the same culture method. The fact that the virus titer of the method of the present invention was higher than that of the conventional method when subculturing was performed under the same conditions means that HAV virus was prepared faster and more stably by the method of the present invention. The difference in virus titer between cell lines is presumed to be due to a difference in cell susceptibility to hepatitis A virus infection, but should be confirmed later through a characteristic study of the seed virus of the present invention. Above all, in the present invention, it is meaningful in that a new virus strain is developed and applied to a vaccine production strain, and its culturing potential was confirmed out of the commercial production of the existing MRC-5-based hepatitis A vaccine.

Figure 12:
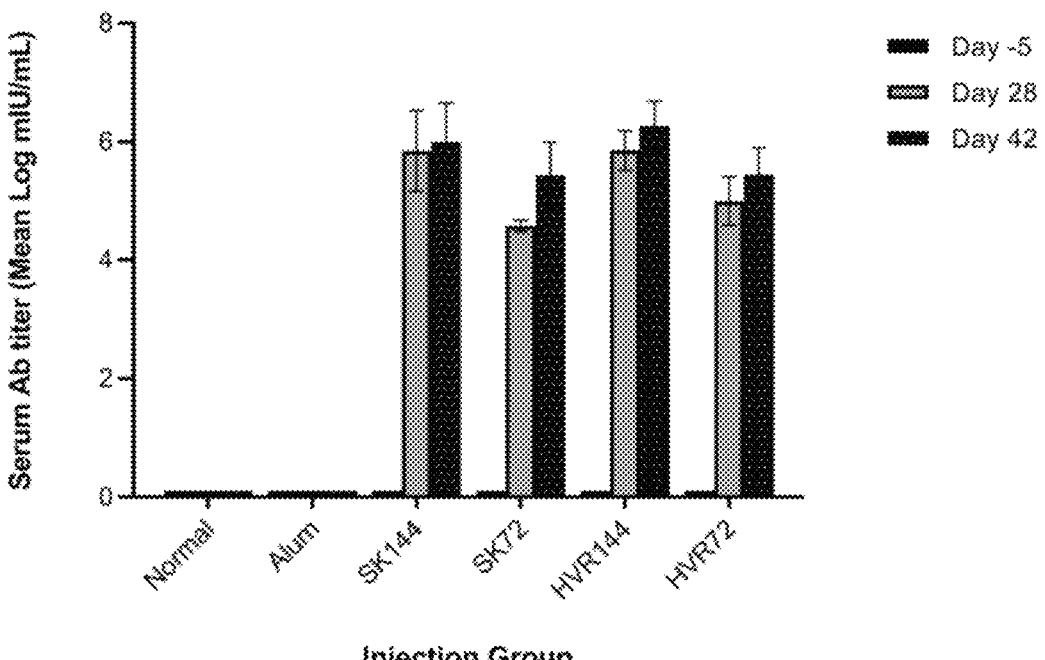
FIG. 12 is a diagram illustrating titers of anti-HAV serum analyzed in the blood of an animal before inoculating an experimental animal with an inactivated antigen or commercial HAV vaccine (HAVRIX®, GSK) of HAV prepared according to the method of the present invention, respectively (Day-5), after inoculating twice at a 2-week interval (Day 28), and after inoculating three times (Day 42). SK144 and SK72 are groups of administering the virus of the present invention at 144 EL.U (3.0 IU) and 72 EL.U (1.5 IU) after purification and inactivation, respectively, and HVR144 and HVR72 are groups of administering commercial product HAVRIX® at 144 EL. U and 72 EL.U. As a negative control for the experiment, a Normal group was administered with saline instead of a viral antigen, and an Alum group was administered only with an alum adjuvant excluding the antigen.
Figure 13:
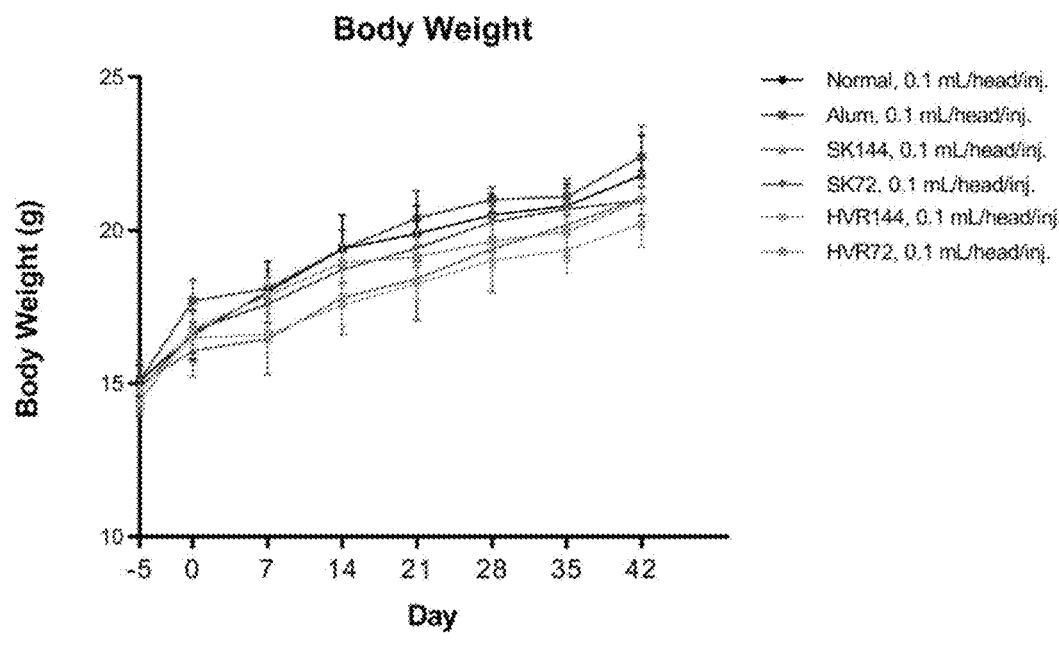
FIG. 13 is a diagram illustrating observing whether an adverse reaction occurs due to antigen inoculation by observing the average body weight of each animal group during the process of performing the experiment according to FIG. 12.

Meanwhile, FIG. 12 shows the production of an antibody against an inactivated antigen administered with serum isolated from the collected mouse whole blood after incubating, purifying, and inactivating the seed virus prepared in the present invention, and then administering the seed virus to mouse experimental animals 3 times at an interval of 2 weeks. FIG. 13 is a diagram illustrating an average value of an animal body weight for each group during the animal experiment. SK144 and SK72 are groups of administering the virus of the present invention at 3 IU (144 EL.U) and 1.5 IU (72 EL.U) after purification and inactivation, respectively, and HVR144 and HVR72 are groups of administering commercial product HAVRIX® at 144 EL.U and 72 EL.U.

Referring to FIG. 12, Day-5 refers to a mouse serum before 5 days of the first administration, Day 28 refers to a serum on day 14 after the second administration, and Day 42 refers to a serum on day 14 after the third administration. A bar graph of each injection group indicates a concentration of anti-HAV antibody (total IgG anti-HAV serum) present in mouse serum harvested on each day. The serum concentration was measured by the antibody titer analysis method described in 12. Animal experiment of the experimental method.

In the Day-5 serum before administration of each administration group, no increase in anti-HAV serum titer was observed in all groups. In the serum analysis on Day 28, it was confirmed that the antibody titer (p>0.9999) between SK144 group (average antibody of 5.742 mIU/mL) and HVR144 group (average antibody of 5.783 mIU/mL) was similar to the antibody titer (p=0.3895) of SK72 group (4.377 mIU/mL) and HVR72 group (4.875 mIU/mL). In the serum analysis on Day 42, it was confirmed that the antibody titer (p=0.8825) between SK144 group (average antibody of 6.002 mIU/mL) and HVR144 group (average antibody of 6.223 mIU/mL) was similar to the antibody titer (p>0.9999) of SK72 group (5.432 mIU/mL) and HVR72 group (5.446 mIU/mL).

FIG. 12 shows that there is no effective difference in the immunological efficacy of the HAV antigen prepared according to the method of the present invention compared to the commercialized hepatitis A vaccine (HAVRIX®). For reference, since a human dose cannot be administered to mice, 1/10 human dose is used and the dose was calculated based on an adult dose of 1440 EL.U/Injection dose and a pediatric dose of 720 EL.U/Injection dose of the commercial hepatitis A vaccine.

Referring to FIG. 13, from the start date to the end date of the animal experiment, adverse reactions of unknown cause, mouse stress, and immediate adverse reactions and weight loss after administration of antigen that may affect immunogenicity measurement were not observed. In addition, even in visual observation, the adverse reaction was also not confirmed by the administered purified inactivated antigen of the present invention and a control material.

INDUSTRIAL APPLICABILITY

According to the method for preparing the hepatitis A virus provided by the present invention, it is possible to prepare hepatitis A virus that is stably amplified within a short period to be very useful for preparing a hepatitis A vaccine. In addition, the method may be used as a source technology for the development of hepatitis A vaccine technology, which has not been developed with domestic technology in Korea.

What is claimed is:

1. A hepatitis A virus gene defined by comprising SEQ ID NO: 1.

2. An expression cassette for preparing hepatitis A virus comprising the hepatitis A virus gene, of claim 1.

3. The expression cassette of claim 2, wherein the expression cassette further comprises a promoter, a hammerhead (HH) ribozyme and a hepatitis delta virus (HDV) ribozyme.

4. The expression cassette of claim 2, wherein the expression cassette comprises SEQ ID NO: 8.

5. A vector comprising the expression cassette of claim 2.

6. A hepatitis A virus comprising the vector of claim 5.

7. A method of preparing a hepatitis A vaccine, the method comprising steps of:
  (a) transfecting a host cell with a vector comprising an expression cassette comprising a hepatitis A virus gene of SEQ ID NO: 1;
  (b) obtaining a virus from the host cell of step (a);
  (c) infecting a host cell with the obtained virus from step (b) and subculturing the host cell; and
  (d) obtaining a virus from the host cell of step (c).

8. The method of claim 7, wherein the expression cassette comprises a CMV promoter, a T7 promoter, a multiple cloning site (MCS), and a hammerhead (HH) ribozyme site in sequence in a 5'-terminal direction of the hepatitis A virus gene, and comprises hepatitis delta virus (HDV) ribozyme, a MCS and a poly-A tail in sequence in a 3'-terminal direction.

9. The method of claim 7, wherein the expression cassette comprises SEQ ID NO: 8.

10. The method of claim 7, wherein the host cell is selected from the group consisting of Vero, MA104, WI-38, BHK-21, CHO, MDCK, Hi5, CEF and Sf9.

11. The method of claim 7, wherein the host cell is a cell adapted to a serum-free medium.

12. The method of claim 7, wherein the subculturing is performed 2 to 30 times.

13. The method of claim 7, wherein in step (d), the host cell exhibits a cytopathic effect in three times or more subculturing.

14. The method of claim 7, wherein the first host cell in step (a) and the second host cell in step (c) are a same cell type.

15. The method of claim 7, further comprising:
  a purification step, an inactivation step, or a purification and inactivation step of the virus after step (d).

16. A hepatitis A virus prepared according to the method of claim 7.

17. A hepatitis A vaccine composition comprising the hepatitis A virus of claim 16 as an active ingredient.

18. The hepatitis A vaccine composition of claim 17, wherein the vaccine is a live vaccine, an attenuated vaccine, or an inactivated vaccine.

19. The hepatitis A vaccine composition of claim 18, further comprising an adjuvant.

20. A kit comprising the hepatitis A vaccine composition according to claim 17.

21. A prefilled syringe filled with the hepatitis A vaccine composition according to claim 17.

22. A method for inhibiting a hepatitis A infection comprising administering an effective dose of a hepatitis A vaccine composition comprising the hepatitis A virus of claim 16 as an active ingredient to a subject in need thereof.

* * * * *